United States Patent
Nobles

(10) Patent No.: US 11,957,331 B2
(45) Date of Patent: Apr. 16, 2024

(54) SUTURING SYSTEMS AND METHODS FOR SUTURING BODY TISSUE

(71) Applicant: HeartStitch, Inc., Fountain Valley, CA (US)

(72) Inventor: Anthony A. Nobles, St. Thomas, VI (US)

(73) Assignee: HeartStitch, Inc., Fountain Valley, CA (US)

(*) Notice: Subject to any disclaimer, the term of this patent is extended or adjusted under 35 U.S.C. 154(b) by 257 days.

(21) Appl. No.: 16/712,014

(22) Filed: Dec. 12, 2019

(65) Prior Publication Data
US 2020/0253599 A1    Aug. 13, 2020

Related U.S. Application Data

(63) Continuation of application No. PCT/US2018/038111, filed on Jun. 18, 2018.

(60) Provisional application No. 62/559,941, filed on Sep. 18, 2017, provisional application No. 62/522,028, filed on Jun. 19, 2017.

(51) Int. Cl.
*A61B 17/04* (2006.01)

(52) U.S. Cl.
CPC .. *A61B 17/0469* (2013.01); *A61B 2017/0472* (2013.01)

(58) Field of Classification Search
CPC ........ A61B 17/0469; A61B 2017/0472; A61B 2017/0475
See application file for complete search history.

(56) References Cited

U.S. PATENT DOCUMENTS

| | | |
|---|---|---|
| 118,683 A | 9/1871 | Bruce |
| 1,064,307 A | 6/1913 | Fleming |

(Continued)

FOREIGN PATENT DOCUMENTS

| | | |
|---|---|---|
| CN | 101495049 | 12/2010 |
| CN | 101257852 | 8/2011 |

(Continued)

OTHER PUBLICATIONS

U.S. Appl. No. 17/812,388, filed Jul. 13, 2022, Nobles et al.

(Continued)

*Primary Examiner* — Ryan J. Severson
*Assistant Examiner* — Andrew P. Restaino
(74) *Attorney, Agent, or Firm* — Knobbe, Martens, Olson & Bear LLP

(57) ABSTRACT

Suturing apparatuses can be configured to suture biological tissue, such as an anatomical valve. The suturing apparatuses can include a suturing device having an elongate shaft having a proximal end and a distal end, one or more tissue grasping arms, and a handle with actuators. The suturing device can further include at least two needles. One of the tissue grasping arms can have at least two suture mounts each loaded with a suture portion. The suture portions on the suture mounts can form a single suture strand. Methods for suturing bodily tissue may be performed with the suturing apparatuses. The tissue grasping arms can grasp tissue therebetween and at least two needles can be deployed toward the suture mounts, engage the suture portions, and be retracted through the tissue. A knot can be tied on the ends of the suture strand retrieved by the needles.

11 Claims, 38 Drawing Sheets

(56) References Cited

U.S. PATENT DOCUMENTS

| | | |
|---|---|---|
| 1,593,347 A | 7/1926 | Nardi |
| 1,822,330 A | 9/1931 | Ainslie |
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,601,564 A | 6/1952 | Smith |
| 2,637,290 A | 5/1953 | Sigoda |
| 2,738,790 A | 3/1956 | Todt, Sr. et al. |
| 2,741,225 A | 4/1956 | Fink |
| 2,741,226 A | 4/1956 | Dietrich et al. |
| 2,748,748 A | 6/1956 | Lovejoy |
| 2,790,422 A | 4/1957 | Grumbach |
| 2,849,002 A | 8/1958 | Oddo |
| 2,945,460 A | 7/1960 | Kagiyama |
| 2,959,172 A | 11/1960 | Held |
| 2,988,055 A | 6/1961 | Platt |
| 3,098,467 A | 7/1963 | Nagele, Jr. |
| 3,107,654 A | 10/1963 | Fehrenback |
| 3,241,554 A | 3/1966 | Coanda |
| 3,260,242 A | 7/1966 | Liguori |
| 3,262,427 A | 7/1966 | Von Arx |
| 3,292,627 A | 12/1966 | Harautuneian |
| 3,294,068 A | 12/1966 | Hechtle |
| 3,301,221 A | 1/1967 | Von Arx |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 3,989,389 A | 11/1976 | Hashimoto et al. |
| 4,022,535 A | 5/1977 | Ritter |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,168,708 A | 9/1979 | Lepley et al. |
| 4,204,541 A | 5/1980 | Kapitanov |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,641,652 A | 2/1987 | Hutterer et al. |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,904,238 A | 2/1990 | Williams |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,946,463 A | 8/1990 | Wright |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,988,339 A | 1/1991 | Vadher |
| 4,994,070 A | 2/1991 | Waters |
| 5,002,531 A | 3/1991 | Bonzel |
| 5,021,059 A | 6/1991 | Kensey et al. |
| 5,037,428 A | 8/1991 | Picha et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,108,421 A | 4/1992 | Fowler |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,152,769 A | 10/1992 | Baber |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,171,259 A | 12/1992 | Inoue |
| 5,174,300 A | 12/1992 | Bales et al. |
| 5,176,691 A | 1/1993 | Pierce |
| 5,192,301 A | 3/1993 | Kamiya et al. |
| 5,196,025 A | 3/1993 | Ranalletta et al. |
| 5,201,760 A | 4/1993 | West |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,254,126 A | 10/1993 | Filipi et al. |
| 5,269,791 A | 12/1993 | Mayzels et al. |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,323,789 A | 6/1994 | Berggren et al. |
| 5,330,446 A | 7/1994 | Weldon et al. |
| 5,330,497 A | 7/1994 | Freitas et al. |

(56) References Cited

U.S. PATENT DOCUMENTS

| | | |
|---|---|---|
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,387,221 A | 2/1995 | Bisgaard |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,568 A | 12/1995 | Scott |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,503,634 A | 4/1996 | Christy |
| 5,507,754 A | 4/1996 | Green et al. |
| 5,507,755 A | 4/1996 | Gresl et al. |
| 5,507,757 A | 4/1996 | Sauer et al. |
| 5,514,159 A | 5/1996 | Matula et al. |
| 5,520,609 A | 5/1996 | Moll et al. |
| 5,520,702 A | 5/1996 | Sauer et al. |
| 5,520,703 A | 5/1996 | Essig et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,618 A | 8/1996 | Fleenor et al. |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,685 A | 10/1996 | Mollenauer et al. |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,571,167 A | 11/1996 | Maginot |
| 5,573,540 A | 11/1996 | Yoon |
| 5,578,044 A | 11/1996 | Gordon et al. |
| 5,584,803 A | 12/1996 | Stevens et al. |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,662,664 A | 9/1997 | Gordon et al. |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Ambrosio |
| 5,700,273 A | 12/1997 | Buelna et al. |
| 5,700,276 A | 12/1997 | Benecke |
| 5,700,277 A | 12/1997 | Nash et al. |
| 5,707,379 A | 1/1998 | Fleenor et al. |
| 5,709,693 A | 1/1998 | Taylor |
| 5,713,910 A | 2/1998 | Gordon et al. |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,728,133 A | 3/1998 | Kontos |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,836,956 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |

(56) References Cited

U.S. PATENT DOCUMENTS

| | | |
|---|---|---|
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,868,764 A | 2/1999 | Rosengart |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,924,424 A | 7/1999 | Stevens et al. |
| 5,925,054 A | 7/1999 | Taylor et al. |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,947,919 A | 9/1999 | Krueger et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,042,601 A | 3/2000 | Smith |
| 6,048,351 A | 4/2000 | Gordon et al. |
| 6,056,760 A | 5/2000 | Koike |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,276 A | 6/2000 | Kontos |
| 6,077,277 A | 6/2000 | Mollenauer et al. |
| 6,077,279 A | 6/2000 | Kontos |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,165,196 A | 12/2000 | Stack et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,254,620 B1 | 7/2001 | Koh et al. |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,443,962 B1 | 9/2002 | Gaber |
| 6,468,293 B2 | 10/2002 | Bonutti et al. |
| 6,482,171 B1 | 11/2002 | Corvi et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,695,859 B1 | 2/2004 | Golden et al. |
| 6,712,831 B1 | 3/2004 | Kaplan et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,840,246 B2 | 1/2005 | Downing |
| 6,978,176 B2 | 1/2005 | Lattouf |
| 6,855,157 B2 | 2/2005 | Foerster et al. |
| 6,887,249 B1 | 5/2005 | Houser et al. |
| 6,893,448 B2 | 5/2005 | O'Quinn et al. |
| 6,896,686 B2 | 5/2005 | Weber |
| 6,911,034 B2 | 6/2005 | Nobles et al. |
| 6,913,600 B2 | 7/2005 | Valley et al. |
| 6,932,827 B2 | 8/2005 | Cole |
| 6,936,057 B1 | 8/2005 | Nobles |
| 6,964,668 B2 | 11/2005 | Modesitt et al. |
| 6,991,635 B2 | 1/2006 | Takamoto |
| 7,004,952 B2 | 2/2006 | Nobles et al. |
| 7,063,710 B2 | 6/2006 | Takamoto |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,232,448 B2 | 6/2007 | Battles |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,544,199 B2 | 6/2009 | Bain |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,704,261 B2 | 4/2010 | Sakamoto |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |

(56) References Cited

U.S. PATENT DOCUMENTS

| | | |
|---|---|---|
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,935,128 B2 | 5/2011 | Rioux |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,100,922 B2 | 1/2012 | Griffith |
| 8,105,355 B2 | 1/2012 | Page et al. |
| 8,152,821 B2 | 4/2012 | Gambale |
| 8,197,497 B2 | 6/2012 | Nobles et al. |
| 8,197,510 B2 | 6/2012 | Nobles |
| 8,202,281 B2 | 6/2012 | Voss |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,313,498 B2 | 11/2012 | Pantages |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,465,500 B2 | 6/2013 | Speziali |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,679,139 B2 | 3/2014 | Aguirre et al. |
| 8,709,020 B2 | 4/2014 | Nobles |
| 8,728,105 B2 | 5/2014 | Aguirre |
| 8,758,370 B2 | 6/2014 | Shikhman et al. |
| 8,771,296 B2 | 7/2014 | Nobles et al. |
| 9,078,752 B2 | 7/2015 | Hasenkam |
| 9,125,632 B2 | 9/2015 | Loulmet |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,572,667 B2 | 2/2017 | Solem |
| 9,649,106 B2 | 5/2017 | Nobles et al. |
| 9,706,988 B2 | 7/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 10,420,545 B2 | 9/2019 | Nobles et al. |
| 10,512,458 B2 | 12/2019 | Nobles |
| 10,610,216 B2 | 4/2020 | Nobles et al. |
| 10,624,629 B2 | 4/2020 | Nobles et al. |
| 10,687,801 B2 | 6/2020 | Nobles et al. |
| 10,758,223 B2 | 9/2020 | Nobles et al. |
| 10,828,022 B2 | 11/2020 | Nobles et al. |
| 11,051,802 B2 | 7/2021 | Nobles et al. |
| 11,197,661 B2 | 12/2021 | Nobles et al. |
| 11,202,624 B2 | 12/2021 | Nobles |
| 11,395,658 B2 | 7/2022 | Nobles et al. |
| 11,591,554 B2 | 2/2023 | Nobles |
| 11,744,576 B2 | 9/2023 | Nobles et al. |
| 11,779,324 B2 | 10/2023 | Nobles |
| 2001/0021854 A1 | 9/2001 | Donnez et al. |
| 2001/0031973 A1 | 10/2001 | Nobles et al. |
| 2001/0049492 A1 | 12/2001 | Frazier et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0096183 A1 | 7/2002 | Stevens et al. |
| 2002/0111653 A1 | 8/2002 | Foerster |
| 2002/0128598 A1 | 9/2002 | Nobles |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0120287 A1 | 6/2003 | Gross et al. |
| 2003/0144673 A1 | 7/2003 | Onuki et al. |
| 2003/0195539 A1 | 10/2003 | Attinger et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0068273 A1 | 4/2004 | Fariss et al. |
| 2004/0102797 A1 | 5/2004 | Golden et al. |
| 2004/0153116 A1 | 8/2004 | Nobles |
| 2004/0236356 A1 | 11/2004 | Rioux et al. |
| 2004/0260298 A1 | 12/2004 | Kaiseer et al. |
| 2005/0033361 A1 | 2/2005 | Galdonik et al. |
| 2005/0059984 A1 | 3/2005 | Chanduszko |
| 2005/0070923 A1 | 3/2005 | McIntosh |
| 2005/0149066 A1 | 7/2005 | Stafford |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2005/0288690 A1 | 12/2005 | Bourque et al. |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0155245 A1 | 7/2006 | Woehr |
| 2006/0195120 A1 | 8/2006 | Nobles et al. |
| 2006/0206146 A1 | 9/2006 | Tenerz |
| 2006/0248691 A1 | 11/2006 | Rosemann |
| 2006/0259046 A1 | 11/2006 | de la Torre |
| 2006/0265010 A1 | 11/2006 | Paraschac et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0010829 A1 | 1/2007 | Nobles et al. |
| 2007/0043385 A1 | 2/2007 | Nobles et al. |
| 2007/0049952 A1 | 3/2007 | Weiss |
| 2007/0060930 A1 | 3/2007 | Hamilton et al. |
| 2007/0106310 A1 | 5/2007 | Goldin et al. |
| 2007/0118151 A1* | 5/2007 | Davidson .......... A61B 17/0469 606/151 |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0027468 A1 | 1/2008 | Fenton |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0091220 A1 | 4/2008 | Chu |
| 2008/0097482 A1 | 4/2008 | Bain et al. |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0062851 A1 | 3/2009 | Rosenblatt |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |

(56) References Cited

U.S. PATENT DOCUMENTS

| | | |
|---|---|---|
| 2009/0299406 A1* | 12/2009 | Swain ............... A61B 17/0469 606/139 |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0185234 A1 | 7/2010 | Fortson et al. |
| 2010/0210899 A1 | 8/2010 | Schankereli |
| 2010/0280530 A1 | 11/2010 | Hashiba |
| 2011/0011917 A1 | 1/2011 | Loulmet |
| 2011/0071626 A1 | 3/2011 | Wright |
| 2011/0190793 A1 | 8/2011 | Nobles et al. |
| 2011/0202077 A1 | 8/2011 | Chin et al. |
| 2011/0208214 A1 | 8/2011 | Poo et al. |
| 2011/0224720 A1 | 9/2011 | Kassab et al. |
| 2011/0251627 A1 | 10/2011 | Hamilton et al. |
| 2011/0288637 A1 | 11/2011 | De Marchena |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2012/0303046 A1 | 11/2012 | Stone et al. |
| 2013/0103056 A1 | 4/2013 | Chu |
| 2013/0253542 A1 | 9/2013 | Ostgrovsky et al. |
| 2013/0261645 A1 | 10/2013 | Nobles et al. |
| 2013/0324800 A1 | 12/2013 | Cahill |
| 2014/0148825 A1* | 5/2014 | Nobles ............... A61B 17/0057 606/145 |
| 2014/0194906 A1 | 7/2014 | Topper |
| 2014/0276975 A1 | 9/2014 | Argentine |
| 2014/0276979 A1 | 9/2014 | Sauer |
| 2014/0309670 A1 | 10/2014 | Bakos et al. |
| 2014/0371790 A1 | 12/2014 | Hatch |
| 2014/0379006 A1 | 12/2014 | Sutherland et al. |
| 2015/0100071 A1 | 4/2015 | Phillips et al. |
| 2015/0196294 A1 | 7/2015 | Murillo |
| 2015/0313620 A1 | 11/2015 | Suri |
| 2015/0359531 A1 | 12/2015 | Sauer |
| 2016/0045315 A1* | 2/2016 | Vola ............... A61B 17/068 623/2.11 |
| 2016/0143737 A1 | 5/2016 | Zentgraf |
| 2016/0151064 A1 | 6/2016 | Nobles |
| 2016/0324636 A1 | 11/2016 | Rourke |
| 2016/0345961 A1 | 12/2016 | Sauer |
| 2017/0035425 A1 | 2/2017 | Fegelman et al. |
| 2017/0049440 A1 | 2/2017 | Sauer |
| 2017/0049451 A1 | 2/2017 | Hausen |
| 2017/0296168 A1 | 4/2017 | Nobles et al. |
| 2017/0128059 A1 | 5/2017 | Coe et al. |
| 2018/0311043 A1 | 11/2018 | Neustadter |
| 2019/0029672 A1 | 1/2019 | Nobles et al. |
| 2019/0150903 A1 | 5/2019 | Nobles |
| 2019/0239880 A1 | 8/2019 | Nobles |
| 2019/0388084 A1 | 12/2019 | Nobles et al. |
| 2020/0214694 A1 | 7/2020 | Nobles |
| 2020/0253602 A1 | 8/2020 | Nobles |
| 2020/0268373 A1 | 8/2020 | Nobles |
| 2020/0281584 A1 | 9/2020 | Nobles |
| 2021/0045735 A1 | 2/2021 | Nobles |
| 2021/0219974 A1 | 7/2021 | Nobles |
| 2021/0386420 A1 | 12/2021 | Nobles |
| 2022/0280149 A1 | 9/2022 | Nobles |
| 2022/0313229 A1 | 10/2022 | Nobles |
| 2023/0279319 A1 | 9/2023 | Nobles |

FOREIGN PATENT DOCUMENTS

| | | |
|---|---|---|
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 0 941 698 | 5/2005 |
| EP | 0 870 486 | 11/2005 |
| EP | 0 983 027 | 12/2005 |
| EP | 1 852 071 | 11/2007 |
| EP | 1 987 779 | 11/2008 |
| EP | 2 572 649 | 3/2013 |
| EP | 2 413 809 | 10/2014 |
| EP | 3 644 194 | 12/2022 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 04088978 B2 | 5/2008 |
| JP | 2008-541857 | 11/2008 |
| JP | 2008-546454 | 12/2008 |
| JP | 2010-522625 | 7/2010 |
| JP | 2011-067251 | 4/2011 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/25254 | 5/1999 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 08/121738 | 10/2008 |
| WO | WO 09/081396 | 7/2009 |
| WO | WO 09/137766 | 11/2009 |
| WO | WO 11/047201 | 4/2011 |
| WO | WO 11/094619 | 8/2011 |
| WO | WO 11/137224 | 11/2011 |
| WO | WO 11/156782 | 12/2011 |
| WO | WO 12/012336 | 1/2012 |
| WO | WO 12/142338 | 10/2012 |
| WO | WO 13/027209 | 2/2013 |
| WO | WO 13/142487 | 9/2013 |
| WO | WO 13/170081 | 11/2013 |
| WO | WO 15/002815 | 1/2015 |
| WO | WO 15/085145 | 6/2015 |
| WO | WO 17/180092 | 10/2017 |

(56) References Cited

FOREIGN PATENT DOCUMENTS

| WO | WO 18/236822 | 12/2018 |
|---|---|---|
| WO | WO 19/035095 | 2/2019 |
| WO | WO 19/051379 | 3/2019 |
| WO | WO 19/055433 | 3/2019 |

OTHER PUBLICATIONS

U.S. Appl. No. 18/114,875, filed Feb. 27, 2023, Nobles.
Joshi, Devang J., et al., A Novel Minimal Access Cardiac Surgery Automated Suturing Device with a Needle Sheath to Minimize the Risk of Needle-Stick Injuries, Annual Meeting Posters, IS ISMICS annual scientific meeting, Jun. 3-6, 2015; as available on Jul. 25, 2015 by the Wayback Machine Internet Archive, accessed on Mar. 16, 2022, 11 pages https://web.archive.org/web/20150625011714/https://meetings.ismics.org/abstracts/2015/P21.cgi.
LSI Solutions, RD180 product device page as available on Mar. 20, 2016 by the Wayback Machine Internet Archive, accessed on Mar. 16, 2022, 2 pages https://web.archive.org/web/20160320182253/http://www.Isisolutions.com/rd180deviceanatomy.
Ozawa, Soji, et al., (2005). New endoscopic treatments for gastroesophageal reflux disease. Annals of thoracic and cardiovascular surgery: official journal of the Association of Thoracic and Cardiovascular Surgeons of Asia. 11. 146-53.
European Partial Search Report, re EP Application No. 22159285, dated Dec. 2, 2022, 8 pages.
Advances in Vascular Surgery, by John S. Najarian, M.D. and John P. Delaney, M.D., copyright 1983 by Year Book Publishers, Inc. at pp. 94, 95, 96, and 224.
Cardio Medical Solutions, Inc. brochure titled: "Baladi Inverter for Clamp less Surgery"—Undated, 4 pages.
Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.
Current Therapy in Vascular Surgery, 2nd edition, by Calvin B. Ernst, M.D. and James C. Stanley, M.D., copyright 1991 By B.C. Decker, Inc., at pp. A and 140.
Eskuri, A., The Design of a Minimally Invasive Vascular Suturing Device, Thesis submitted to Rose-Hulman Institute of Technology, Nov. 1999.
Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.
Nursing the Open-Heart Surgery Patient, By Mary Jo Aspinall, R.N., M.N., copyright 1973 by McGraw Hill, Inc., at pp. 216 and 231.
Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.
Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.
Techniques in Vascular Surgery, by Denton A. Cooley, MD. and Don C. Wukasch, MD., copyright 1979 by WB. Saunders Co., at pp. 38, 57, 86, 134, 156, and 184.
The problem: Closing wounds in deep areas during laparoscopic operations The solution: REMA Medizintechnik GmbH (no date), 7 pages.
Vascular Access, Principles and Practice, 3rd edition, by Samuel Eric Wilson, MD., copyright 1996, 1988, 1980 by Mosby-Year Book, Inc., pp. 89 and 159.
Vascular and Endovascular Surgery, by Jonathan D. Beard and Peter Gainers, copyright 1998 by W. B. Saunders Co., Ltd, p. 414.
Vascular Surgery, 3rd edition, vol. 1, by Robert B. Rutherford, MD., copyright 1989, 1984, 1976 By W. B.SaundersCo., at pp. 347, 348, 354, 594, 607, 622, 675, 677, 680, 698, 700, 721, 727, 735, and 829.
Vascular Surgery, 4th edition by Robert B. Rutherford, MD., copyright 1995,1989,1976, by W.B. Saunders Co., vol. 1, at pp. 400-404, 661, and A.
Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.
Vascular Surgery, by Robert B. Rutherford, M.D. copyright1977 by WB. Saunders Co., at pp. 334 and 817.
International Search Report and Written Opinion of PCT/US2018/038111, dated Nov. 30, 2018, 20 pages.
International Preliminary Report on Patentability of PCT/US2018/038111, dated Dec. 24, 2019, 11 pages.
European Extended Search Report, re EP Application No. 22159285, dated Mar. 6, 2023, 11 pages.

* cited by examiner

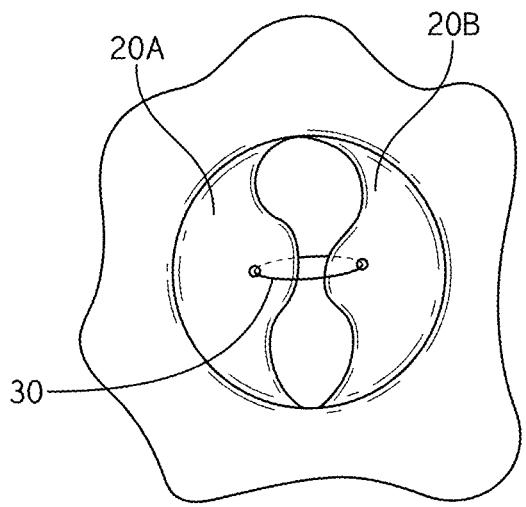 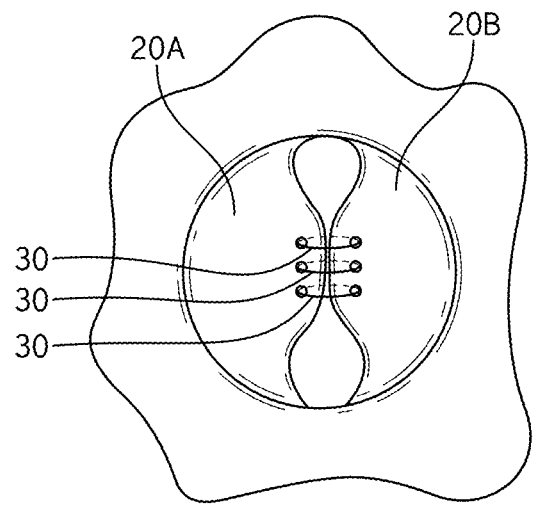
FIG. 2A  FIG. 2B
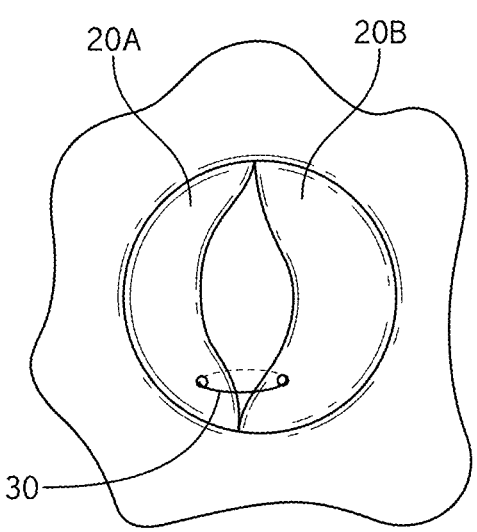 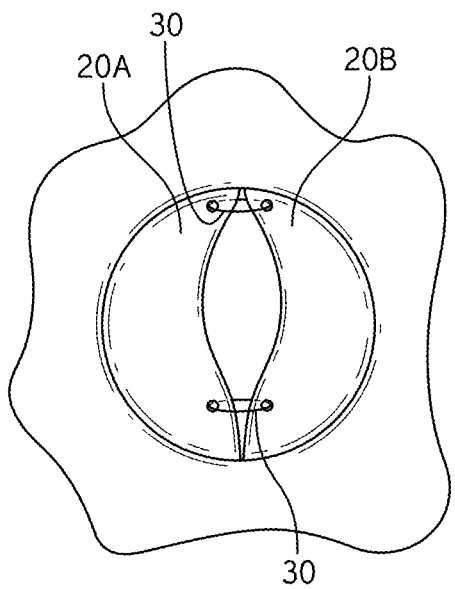
FIG. 2C  FIG. 2D

SUTURING SYSTEMS AND METHODS FOR SUTURING BODY TISSUE

PRIORITY CLAIM AND INCORPORATION BY REFERENCE

This application claims the benefit under 35 U.S.C. § 120 and 35 U.S.C. § 365(c) as a continuation of International Application No. PCT/US2018/038111, designating the United States, with an international filing date of Jun. 18, 2018, titled "SUTURING SYSTEMS AND METHODS FOR SUTURING BODY TISSUE," which claims the benefit under 35 U.S.C. § 119(e) of U.S. Provisional Patent Application No. 62/522,028, filed on Jun. 19, 2017 and U.S. Provisional Patent Application No. 62/559,941, filed on Sep. 18, 2017, which are hereby incorporated by reference herein in their entireties, forming part of the present disclosure. Any feature, structure, material, method, or step that is described and/or illustrated in any embodiment in any of the foregoing provisional patent applications can be used with or instead of any feature, structure, material, method, or step that is described and/or illustrated in the following paragraphs of this specification or the accompanying drawings.

TECHNICAL FIELD

The present disclosure relates to suturing devices and methods. Some embodiments relate to suturing devices and methods for suturing an anatomical structure, such as mitral valves or other valves of the heart or elsewhere in the body.

BACKGROUND

Health practitioners frequently use sutures to close various openings such as cuts, punctures, and incisions in various places in the human body. Generally, sutures are convenient to use and function properly to hold openings in biological tissue closed, thereby aiding in blood clotting, healing, and prevention of scarring.

Some heart valves may be weakened or stretched, or may have other structural defects, such as congenital defects, that cause them to close improperly. Such conditions can lead to reverse flow of the blood. This condition, referred to as regurgitation, incompetence, or insufficiency, can reduce oxygenated blood flow in the normal direction and oxygen supply to the patient. Regurgitation can cause the heart to work harder to compensate for backflow of blood through these valves, which can lead to enlargement of the heart, and/or reduction in cardiac performance. While the tricuspid valve and the pulmonary valve may present these or similar conditions, the mitral valve and aortic valve more frequently demonstrate these conditions.

A number of procedures have been developed to repair valves that do not close properly. Among these procedures is the Alfieri technique, sometimes called edge-to-edge repair, which involves suturing edges of the leaflets and pulling the leaflets closer together. A patch or pledget is sometimes applied to leaflets that have openings therein to reduce tearing of the suture through soft tissue. In some instances, leaflets can be reshaped by removing a section of the leaflet that is to be treated and the surrounding portion of the leaflet is sutured closed. Some valves are treated by attaching a ring around the outside of the malfunctioning valve. Other valves may be replaced with biological or mechanical replacements.

There are some circumstances under which the use of conventional sutures and suturing methods require invasive and prolonged procedures that subject a patient to risk of infection, delays in recovery, increases in pain, and other complications. There are other circumstances under which it is not feasible to use conventional sutures and suturing methods to close an opening. One type of invasive procedure is an open-heart surgery, which requires opening a patient's chest, stopping the patient's heart and routing blood through a heart-lung machine. The procedures can also be time-consuming, at least in part because the suturing technique requires complicated steps. Examples of such procedures include the open surgery Alfieri technique and the MitraClip procedure for mitral regurgitation. These suturing procedures can be traumatic to the patient. The success of these procedures can also be highly dependent on the skill of the user.

SUMMARY OF THE DISCLOSURE

Embodiments of the present disclosure provide less-invasive, easy-to-use, and efficient suturing devices, systems and methods for suturing body tissues. The suturing devices, systems and methods can be applied in percutaneous surgeries, including but not limited to transapical mitral valve repair and laparoscopic procedures. The suturing devices and methods can be used to suture any type of body tissue, for example, the mitral valves, the tricuspid valves, other types of valves, and blood vessels.

A suturing apparatus for suturing biological tissue can comprise a suturing device. The device can comprise an elongate housing having a proximal end and a distal end; a handle coupled to the proximal end of the elongate housing; at least one pair of tissue grasping arms coupled to the distal end of the elongate housing, the handle configured to cause the at least one pair of tissue grasping arms to transition between an open configuration and a closed configuration, wherein the at least one pair of tissue grasping arms in the closed configuration can be configured to grasp tissue to be sutured therebetween with a first of the tissue grasping arms being provided on a first side of the tissue and a second of the tissue grasping arms being positioned on a second side of the tissue opposite the first side, wherein the second of the tissue grasping arms can comprise a tissue-facing side, an opposite side, and at least first and second suture mounts, and wherein the first of the tissue grasping arms can be dimensioned to allow access to the at least first and second suture mounts of the second of the tissue grasping arms from the tissue-facing side of the second of the tissue grasping arms; at least first and second needle lumens extending along a length of at least a portion of the elongate housing, each of the first and second needle lumens located on a substantially diametrically opposite side of the elongate housing from the second of the tissue grasping arms; and at least first and second needles, the first needle being housed within the first needle lumen, the second needle being housed within the second needle lumen, wherein when the at least one pair of tissue grasping arms is in the closed configuration grasping tissue therebetween, the handle can be configured to cause the at least first and second needles to move from the at least first and second needle lumens, respectively, to the second of the tissue grasping arms such that the first and second needles can penetrate through the grasped tissue and catch suture portions each located at the first and second suture mounts, respectively, and wherein the handle can be further configured to cause the at least first and second needles to retract from the at least first and second suture mounts, carrying the suture portions back through the grasped tissue, and back to the at least first and second needle lumens.

According to some embodiments of a suturing apparatus for suturing biological tissue, the at least first and second needle lumens can have a first needle guide track and a second needle track respectively, each of the first and second needle guide tracks comprising an angled surface extending toward a central longitudinal axis of the elongate housing in a proximal to distal direction.

According to some embodiments of a suturing apparatus for suturing biological tissue, the at least one pair of tissue grasping arms can extend generally distally from the elongate housing in the open and closed configurations, the at least one pair of tissue grasping arms being substantially parallel to each other and to the longitudinal axis of the elongate housing in the closed configuration.

According to some embodiments of a suturing apparatus for suturing biological tissue, the at least first and second suture mounts can each comprise a lumen at an angle such that the first and second needle guide tracks and the lumens of the at least first and second suture mounts can be substantially coaxial when the at least one pair of tissue grasping arms are in the closed configuration.

According to some embodiments of a suturing apparatus for suturing biological tissue, the at least first and second needle lumens can be located in a needle guide sheath extending along a length of at least a portion of the elongate housing, the needle guide sheath comprising a hypotube at a distal end of the needle guide sheath, the hypotube being hingedly coupled at or near the distal end of the elongate housing at a joint, wherein when the at least one pair of tissue grasping arms is in the closed configuration grasping tissue therebetween, the needle guide sheath can be configured to bulge radially outwardly from a central longitudinal axis of the elongate housing when under a distal force, thereby causing swinging of a distal opening of each of the at least first and second needle lumens, pivoted at the joint, toward the at least one pair of tissue grasping arms so as to align the at least first and second needles with the at least first and second suture mounts.

According to some embodiments of a suturing apparatus for suturing biological tissue, the needle guide sheath can comprise a hinged joint along its length and buckles at the hinged joint along its length under the distal force.

According to some embodiments of a suturing apparatus for suturing biological tissue, a distal portion of the elongate housing can comprise one or more joints, wherein when the at least one pair of tissue grasping arms is in the closed configuration, the handle can be configured to cause the at least one pair of tissue grasping arms and/or the distal portion of the elongate housing to pivotally rotate at the one or more joints so as to align the at least first and second suture mounts with the at least first and second needle lumens.

According to some embodiments of a suturing apparatus for suturing biological tissue, when the at least first and second suture mounts are aligned with the at least first and second needle lumens, the first tissue grasping arm can be substantially perpendicular to the at least first and second needle lumens.

According to some embodiments of a suturing apparatus for suturing biological tissue, the direction of movement of the first and second needles can be parallel to a longitudinal axis of the elongate housing.

According to some embodiments of a suturing apparatus for suturing biological tissue, a distal portion of the elongate housing can comprise two joints.

According to some embodiments of a suturing apparatus for suturing biological tissue, the distal portion of the elongate shaft can comprise one joint located at the distal end of the elongate shaft between the elongate shaft and the at least one pair of tissue grasping arms, the elongate shaft further comprising a bifurcated needle lumens portion running alongside the distal portion of the elongate shaft.

According to some embodiments of a suturing apparatus for suturing biological tissue, the first of the at least one pair of tissue grasping arms can comprise a detent on a side opposite a tissue-facing side, the detent configured to align the first and second needle lumens with the first and second suture mounts respectively.

According to some embodiments of a suturing apparatus for suturing biological tissue, the suturing apparatus can further comprise a knot-tying device.

According to some embodiments of a suturing apparatus for suturing biological tissue, the suturing apparatus can further comprise one or more pledgets configured to be passing along the suture portion.

According to some embodiments of a suturing apparatus for suturing biological tissue, the at least one pair of tissue grasping arms can be configured to grasp native leaflets of a heart valve.

According to some embodiments of a suturing apparatus for suturing biological tissue, the suturing apparatus can comprise two pledgets, one of the two pledgets configured to be drawn into contact with a first leaflet and another one of the two pledgets configured to be drawn into contact with a second leaflet.

According to some embodiments of a suturing apparatus for suturing biological tissue, the suture portions located at the first and second suture mounts can comprise a single suture strand. The at least first and second needle lumens can be configured to allow the first and second needles pass alongside or through the first of the tissue grasping arms.

According to some embodiments of a suturing apparatus for suturing biological tissue, the first of the tissue grasping arm can comprise one or more cut-out portions configured allow passage of the at least first and second needles.

According to some embodiments of a suturing apparatus for suturing biological tissue, the handle can comprise a switch operably connected to the at least one pair of tissue grasping arms and configured to cause the at least one pair of tissue grasping arms to transition between the open and closed configurations.

According to some embodiments of a suturing apparatus for suturing biological tissue, the at least one pair of tissue grasping arms can further comprise a tissue-gripping configuration, wherein a distance between the at least one pair of tissue grasping arms can be smaller than the distance when the at least one pair of tissue grasping arms are in the closed configuration.

According to some embodiments of a suturing apparatus for suturing biological tissue, the handle can comprise an actuator operably connected to the at least first and second needles and configured to deploy and/or retract the at least first and second needles.

According to some embodiments of a suturing apparatus for suturing biological tissue, the actuator can comprise a slide spring-biased into a retracted mode.

According to some embodiments of a suturing apparatus for suturing biological tissue, the at least one pair of tissue grasping arms can comprise a first tissue grasping arm, a second tissue grasping arm, and a central tissue grasping arm.

According to some embodiments of a suturing apparatus for suturing biological tissue, the at least one pair of tissue grasping arms can comprise first and second pairs of tissue grasping arms.

A method of suturing an anatomical valve can comprise steps of grasping adjacent leaflets of the anatomical valve between a first grasping arm and a second grasping arm, wherein the second grasping arm can comprise a first suture mount and second suture mount for holding portions of one or more sutures on a first side of the anatomical valve; advancing a first needle and a second needle through the grasped anatomical leaflets of the anatomical valve from a second side of the anatomical valve opposite to the first side to catch the portions of the one or more sutures held in the first and second suture mounts, respectively; and retracting the first and second needles from the first and second suture mounts to carry the suture portions back through grasped anatomical leaflets such that the one or more sutures extend through the anatomical leaflets.

According to some embodiments of a method of suturing an anatomical valve, the method can further comprise holding the adjacent leaflets between the first and second grasping arms in an orientation parallel to a longitudinal axis of a delivery device carrying the first and second needles and the first and second grasping arms, and delivering the first and second needles at an angle or perpendicular to the longitudinal axis.

According to some embodiments of a method of suturing an anatomical valve, the method can further comprise the adjacent leaflets between the first and second grasping arms in an orientation at an angle or perpendicular to a longitudinal axis of a delivery device carrying the first and second needles and the first and second grasping arms, and delivering the first and second needles parallel to the longitudinal axis.

According to some embodiments of a method of suturing an anatomical valve, the method can further comprise aligning the first and second needles and the adjacent leaflets grasped therebetween with the first and second suture mounts.

According to some embodiments of a method of suturing an anatomical valve, the method can further comprise using the one or more sutures extending through the anatomical leaflets and/or one or more subsequently placed sutures to secure the anatomical leaflets relative to each other by pulling on one or both of the suture ends to draw the suture tight against the first surface of the valve.

According to some embodiments of a method of suturing an anatomical valve, the method can further comprise applying a knot to the one or more sutures and/or the one or more subsequently placed sutures.

According to some embodiments of a method of suturing an anatomical valve, the knot can be applied from the first side of the anatomical valve.

According to some embodiments of a method of suturing an anatomical valve, the anatomical valve may not be grasped when the knot is applied.

According to some embodiments of a method of suturing an anatomical valve, the first and second needles can be deployed and/or retracted simultaneously or sequentially.

According to some embodiments of a method of suturing an anatomical valve, the first and second grasping arms and the needles can be provided on a suturing device controlled by a single handle operated from outside of a patient's body.

According to some embodiments of a method of suturing an anatomical valve, the method can further comprise drawing a first pledget carried by the one or more suture portions extending through the anatomical leaflets into contact with the first surface of the valve.

According to some embodiments of a method of suturing an anatomical valve, the method can further comprise delivering a second pledget along the one or more suture portions extending through the anatomical leaflets into contact with the second surface of the valve.

According to some embodiments of a method of suturing an anatomical valve, the anatomical valve can be a mitral valve.

A suturing apparatus for suturing an anatomical valve can be configured to perform the steps of the method disclosed herein.

A suturing apparatus for suturing biological tissue can comprise a pair of tissue grasping arms configured to transition between an open configuration and a closed configuration, wherein the pair of grasping arms in the closed configuration can be configured to grasp tissue to be sutured there between with a first of the grasping arms being provided on a first side of the tissue and a second of the grasping arms being positioned on a second side of the tissue opposite the first side, wherein the second grasping arm can comprise at least one suture mount configured to hold a portion of a suture on the second side of the tissue; at least one needle configured to be advanced from the first side of the tissue and through the grasped tissue when the pair of tissue grasping arms grasps the tissue to be sutured there between, the at least one needle configured to catch the a portion of suture held by the at least one suture mount on the second side of the tissue and carry the portion of suture back through the grasped tissue to the first side of the grasped tissue; and a handle operably connected to the tissue grasping arms and the at least one needle to advance the at least one needle relative to the pair of tissue grasping arms.

According to some embodiments of a suturing apparatus for suturing biological tissue, the suturing apparatus can be configured for suturing an anatomical valve.

According to some embodiments of a suturing apparatus for suturing biological tissue, the suturing apparatus can further comprise an elongate body extending between the handle, and the at least one needle and the pair of tissue grasping arms.

According to some embodiments of a suturing apparatus for suturing biological tissue, the suturing apparatus can comprise at least two needle lumens extending along a length of at least a portion of the elongate housing. The suturing apparatus can further comprise at least two needles.

According to some embodiments of a suturing apparatus for suturing biological tissue, each of the two needle lumens can include a needle guide track, the needle guide track comprising an angled surface extending toward a central longitudinal axis of the elongate housing in a proximal to distal direction.

According to some embodiments of a suturing apparatus for suturing biological tissue, the pair of tissue grasping arms is configured to hold the tissue parallel or perpendicular to a longitudinal axis of the suturing apparatus.

According to some embodiments of a suturing apparatus for suturing biological tissue, the at least one suture mount can comprise a lumen at an angle such that a portion of the at least one needle and the lumen of the at least one suture mount are substantially aligned when the at least one pair of tissue grasping arms are in the closed configuration.

According to some embodiments of a suturing apparatus for suturing biological tissue, the at least one pair of tissue grasping arms can comprise first and second pairs of tissue grasping arms, the elongate housing comprising a first shaft and a second shaft at the distal end, wherein the first pair of tissue grasping arms can extend distally from a distal end of the first shaft and the second pair of tissue grasping arms can extend distally from a distal end of the second shaft.

According to some embodiments of a suturing apparatus for suturing biological tissue, the first and second pairs of tissue grasping arms can be each configured to capture a leaflet of a valve between the respective arms.

According to some embodiments of a suturing apparatus for suturing biological tissue, the first and second pairs of tissue grasping arms can be configured to move between the open and closed configurations independent of each other.

According to some embodiments of a suturing apparatus for suturing biological tissue, the first or second pair of tissue grasping arms can be configured to be retracted when the second or first pair of the at least one pair of tissue grasping arms are moved to a target leaflet.

According to some embodiments of a suturing apparatus for suturing biological tissue, the first and second shafts can be configured to bend in a plane that intersects lateral sides of the first and second shafts.

According to some embodiments of a suturing apparatus for suturing biological tissue, when each of the first and second pairs of tissue grasping arms have grasped a leaflet between the respective arms, the first and second pairs of tissue grasping arms can be configured to be brought close together.

According to some embodiments of a suturing apparatus for suturing biological tissue, the first and/or second pairs of tissue grasping arms comprise a plurality of slits along a longitudinal axis of the first and/or second shafts.

According to some embodiments of a suturing apparatus for suturing biological tissue, the first and/or second pairs of tissue grasping arms comprise a flexible material.

According to some embodiments of a suturing apparatus for suturing biological tissue, the first and/or second pairs of tissue grasping arms comprise a bi-directional steering feature.

According to some embodiments of a suturing apparatus for suturing biological tissue, the first and/or second pairs of tissue grasping arms comprise a pre-shaped bend.

According to some embodiments of a suturing apparatus for suturing biological tissue, the apparatus can comprise a sleeve slidably disposed around the first and second shaft.

According to some embodiments of a suturing apparatus for suturing biological tissue, the sleeve can be advanced distally to bring the first and second shafts closer together. The sleeve can be configured to constrain the first and second shafts close together when the sleeve is at its distalmost position.

According to some embodiments of a suturing apparatus for suturing biological tissue, a single needle can advance through both the first pair of tissue grasping arms and the second pair of tissue grasping arms.

According to some embodiments of a suturing apparatus for suturing biological tissue, a first needle can advance through the first pair of tissue grasping arms and a second needle can advance through the second pair of tissue grasping arms.

A suturing apparatus comprising one or more of the features described in the foregoing description.

A method of suturing tissue comprising one or more of the features described in the foregoing description.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures:

FIGS. 2A-2D illustrate schematically embodiments of placement of suture through a biological valve.

DETAILED DESCRIPTION

Embodiments of suturing systems and methods for suturing biological tissue are disclosed herein. The suturing apparatuses and their methods of use can be useful in a variety of procedures, such as treating (e.g., closing) wounds and naturally or surgically created apertures or passageways. For example, the suturing devices can be used to treat an anatomical valve, such as a heart valve, including heart valves that may be weakened or stretched, or have other structural defects, such as congenital defects, that cause them to close improperly. One or more suturing devices can be used to treat or repair valves, such as the tricuspid, pulmonary, mitral, and aortic valves, for example. In some suturing procedures, a suturing system including a suturing device disclosed herein can be used to perform procedures such as edge-to-edge repair (like an Alfieri technique), suturing of ventricular spaces, suturing of the chordae, suturing in other locations in the heart, and the like. The suturing system can be used to close or reduce a variety of other tissue openings, lumens, hollow organs or natural or surgically created passageways in the body. The suturing system can also include one or more pledgets. The suturing system can further include a knot-tying/forming device.

Figure 1:
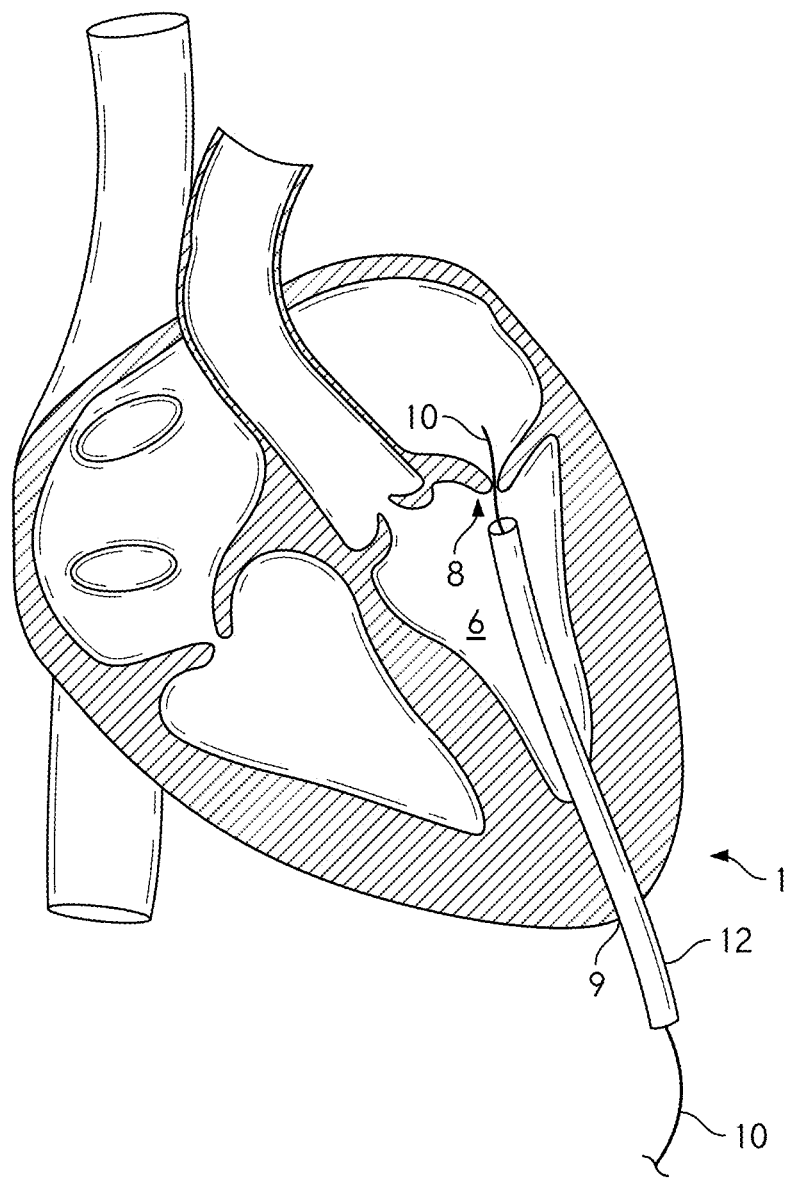
FIG. 1 illustrates schematically a method of providing access to an exemplifying use environment, such as a mitral valve of a heart.

FIG. 1 illustrates an example approach for suturing a mitral valve 8. As shown in FIG. 1, a guide wire 10 is advanced into the left ventricle 6 of the heart through a puncture or incision 9 near an apex 7 of the left ventricle 6. The heart can be accessed through a limited thoracotomy, small trocar puncture, small catheter puncture, or the like. Other access paths may be used. The guide wire 10 can then be further positioned at or near the mitral valve 8. With the guide wire 10 in place, the physician can optionally insert a sheath 12 to the left ventricle 6. The sheath 12 can be placed at or near the mitral valve 8. The suturing device can then be advanced through the lumen of the sheath 12. The suturing device can also be advanced over the guide wire 10 and positioned at or near the mitral valve 8 without the need to insert an introducer sheath 12.

After having gained access to the surgical site, the suturing device can puncture one or more holes through each piece of body tissue to be sutured closed, for example, each of a pair of valve leaflets. The suturing device can pass a single suture strand through these two holes, with two ends of the single suture strand leading outside the patient's body for tying or applying a knot.

As shown in FIGS. 2A-2D, the suturing device disclosed herein can be configured to place one or more suture strands 30 through both the first leaflet 20A and the second leaflet 20B of an opening in a patient's body, either simultaneously or sequentially. The suture strand 30 can be pulled to draw the first leaflet 20A and the second leaflet 20B towards one another before applying a knot to the suture 30. One or more knots can then be applied to the suture strand(s) 30 to hold the leaflets 20A, 20B in proximity to one another.

The suture strand 30 can be placed through the leaflets 20A, 20B at locations selected by the physician to treat a problem of a particular valve or opening. For example, the suture strand 30 can be passed through the leaflets 20A, 20B at locations in or near a central region of the leaflets 20A, 20B as illustrated in FIG. 2A. FIG. 2B illustrates three suture strands 30 passed through the leaflets 20A, 20B in a central region of the leaflets. FIG. 2C illustrates a suture strand 30 being passed through a portion of the leaflets 20A, 20B at or near a periphery of the valve. FIG. 2D illustrates two suture strands 30 being applied to multiple locations between the two leaflets 20A, 20B. The number of suture strands used and the location(s) of where the suture strand(s) is applied can vary based on the problem of the particular valve or opening.

Figure 3:
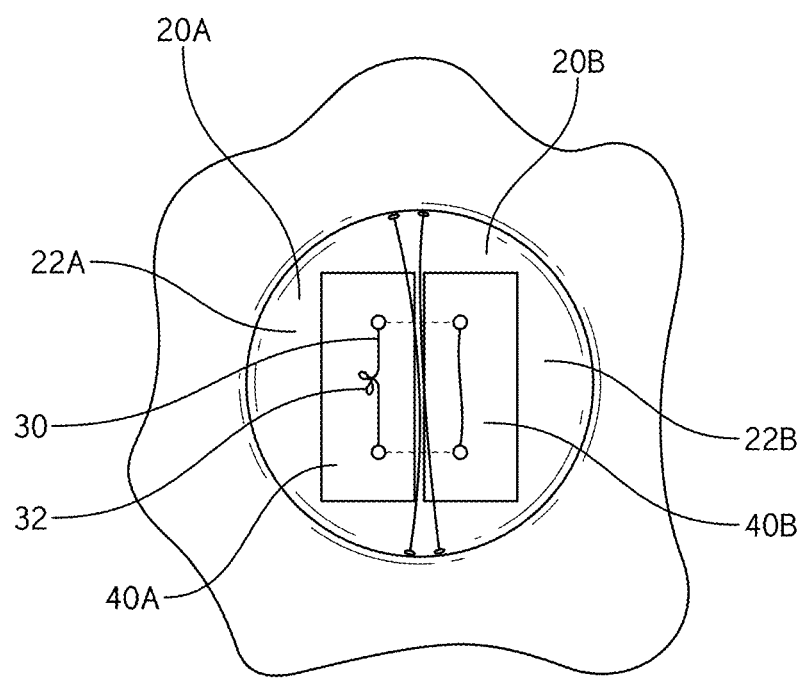
FIG. 3 illustrates schematically an embodiment of placement of suture through a biological valve at two locations spaced from the center of each leaflet using a single suture strand.

As shown in FIG. 3, a single suture strand 30 can be used to close the leaflets 20A, 20B. As will be explained in more detail below, the suture strand 30 can be passed through the leaflets 20A, 20B when the leaflets 20A, 20B are pinched or grasped together. A suturing device facing surface 22A, 22B of each leaflet (for example, leaflet surfaces that face radially outward) can be in contact with the suturing device when the leaflets 20A, 20B are pinched together. Each leaflet can be punctured in one or more locations, for example two locations. For example, in a mitral valve repair procedure, the two locations can be along a coaptation line between the bicuspid leaflets. Two ends of the suture strand 30 can be passed through the two locations respectively from the suturing device facing surface 22B of the leaflet 20B. The two ends of the suture strand 30 can then exit through a suturing device facing surface 22A of the leaflet 20A. A knot 32 can be formed by tying or otherwise joining the two ends of the suture strand 30 on the suturing device facing surface 22A of the leaflet 20A. Although not shown in FIG. 3, the single suture strand 30 can be pulled on both ends to draw the first leaflet 20A and the second leaflet 20B towards one another before the knot is formed.

With continued reference to FIG. 3, the user can pass one or more pledgets 40 along the suture strand 30 such that the one or more pledgets 40 can be applied over the punctured locations on the leaflets 20A, 20B. One pledget 40B can be pre-loaded onto the suture strand 30 before the suturing procedure. The pledget 40B can be drawn against or into contact with the suturing device facing surface 22B of the leaflet 22B. Another pledget 40A can be passed along the suture strand 30 before the knot is tied or applied. The pledgets can reduce teaching of the leaflet tissues at or near the punctured holes. The sutures can also be passed from the leaflet 22A to leaflet 22B, with the knot formed on the suturing device facing surface 22B.

In the case of a mitral repair open surgery, existing technology make it difficult for a user to pass the suture needle across the zone of coaptation of the mitral leaflets percutaneously. The user needs to grab the leaflets along the coaptation line with a tool such as a pair of forceps in one hand, while passing the needle through the leaflets using the other hand. The complexity of the procedure is increased if pledgets are applied to the leaflets. Specifically, one pledget needs to be applied to the ventricular side of one mitral leaflet after the needle has cross both leaflets, and another pledget needs to be applied to the ventricular side of the other mitral leaflets after the needle crosses back through the leaflets. These techniques are time-consuming, complicated, and the outcome can be highly dependent on the skill of the user.

Embodiments of the present disclosure provide suturing devices, systems, and methods that can be used to suture body tissues in a less invasive manner that require fewer steps, and deliver more predictable surgical outcomes than current suturing devices and techniques. Access to the body tissue can be through a percutaneous approach or other less invasive approach than used for open surgery, though the devices, systems and methods can be used in open surgery as well. Embodiments of the suturing devices can include one or more pairs of tissue grasping arms for capturing and holding together body tissues.

The below described suturing devices are intended to illustrate some examples of features found in a suturing device that can be incorporated with the below description. However, other suturing devices can be used as well, such as described in U.S. Pat. Nos. 6,117,144, 6,562,052, 8,246,636, 9,131,938, 9,326,764, 9,642,616, 9,649,106, and 9,706,988, U.S. Pat. Pub. Nos. 2011/0190793, 2016/0151064, and 2016/0302787, and Int'l. Pat. App. No. PCT/US2016/026965, the entirety of each of which is hereby incorporated by reference, which illustrate suturing devices and methods having other features that may be utilized with embodiments described in this disclosure, such as fewer or greater number of arms and/or needles, needles that move in a distal-to-proximal direction, suture spools, separate insertable elongate bodies for suturing, directed needles, curved needles, needle carriers, etc.

Suturing Device Overview

FIGS. 4A-11 illustrate an embodiment of a suturing device 100 configured to suture an anatomical valve or an opening in body tissue, such as a heart valve, without the need of an open surgery. While the device 100 will be described with reference to suturing an anatomical valve, such as a heart valve, the device 100 could be used to suture other biological tissue and implantable materials. The suturing device 100 can include a tissue-engaging distal assembly including first and second tissue grasping arms 130, 140, an elongate housing or shaft 110 having a longitudinal axis, and a handle 120. The elongate housing 110 can have a proximal end 102 and a distal end 103 on opposite ends of the longitudinal axis. The distal end 103 can be coupled to or incorporate the first and second tissue grasping arms 130, 140. The proximal end 102 can be coupled to the handle 120. Although the elongate housing 110 is depicted as having a similar length as the handle 120, the elongate housing 110 can be much longer so as to be advanced through the lumen of the sheath 12 in FIG. 1 to deliver the tissue-engaging distal assembly to a suturing site. The elongate housing 110 can also be flexible. The distal end 103 of the elongate housing 110 can be steerable in two planes or omni-directionally.

Figure 4A:
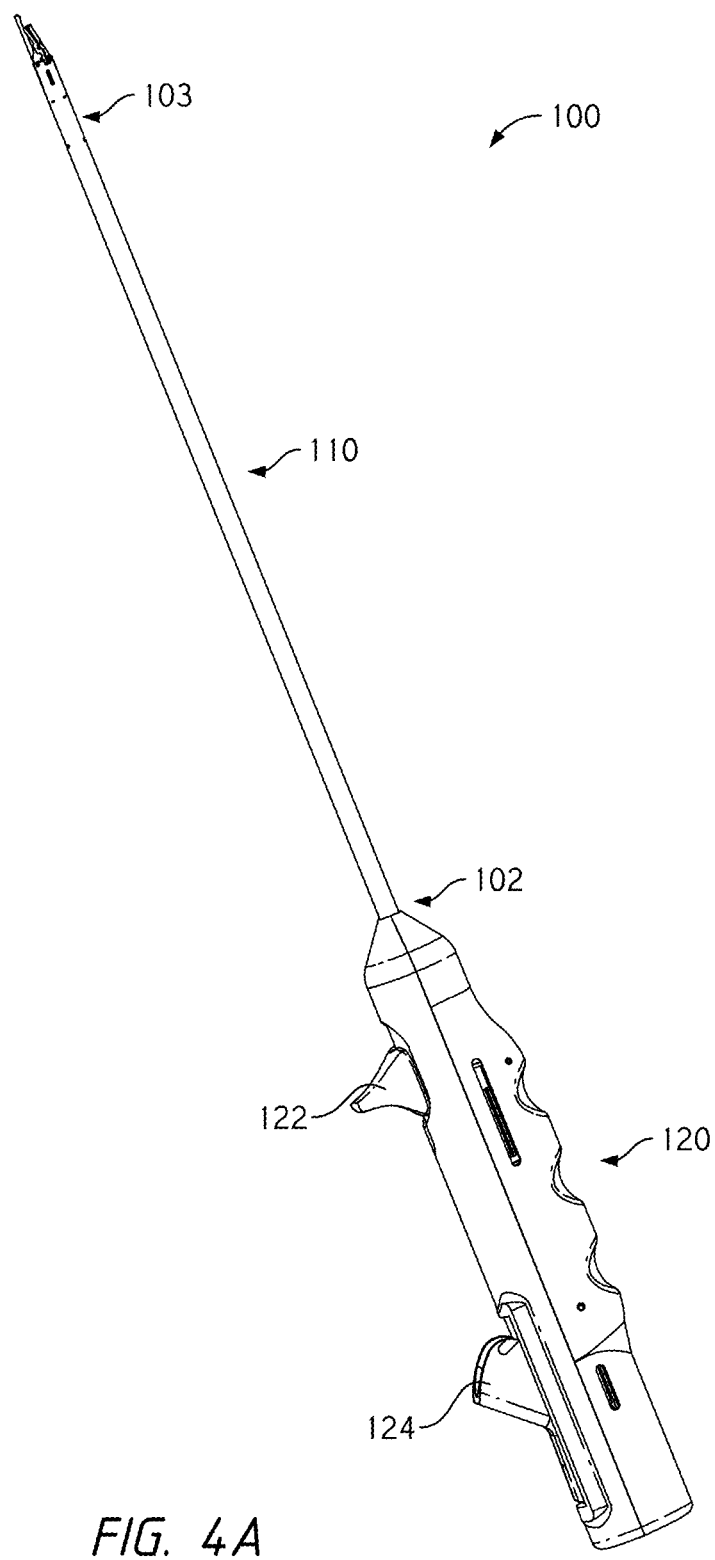
FIG. 4A illustrates a perspective view of an embodiment of a suturing device in a closed configuration.
Figures 4B, 5:
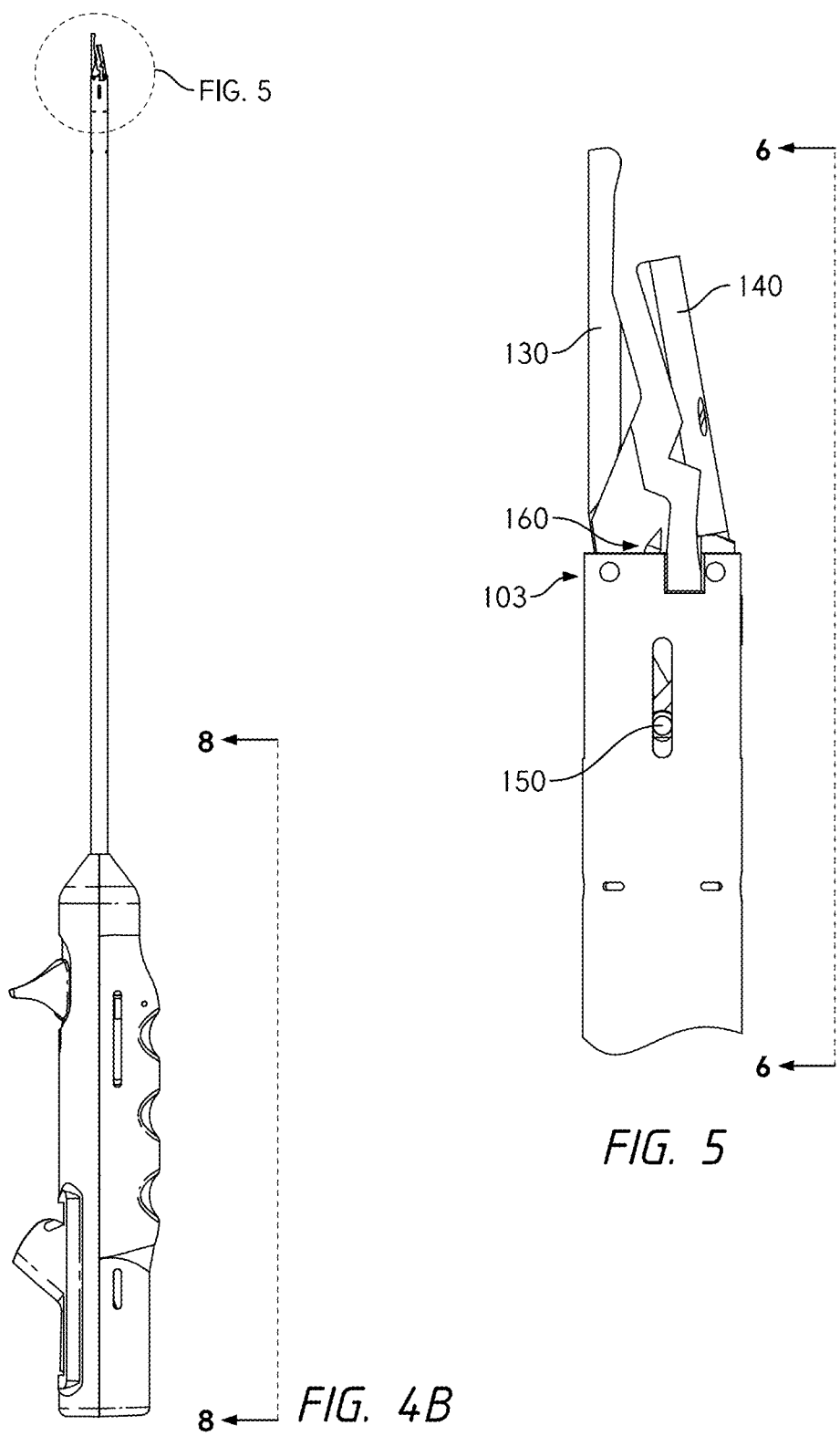
FIG. 4B illustrates a side view of the embodiment of the suturing device of FIG. 4A.
FIG. 5 illustrates an enlarged side view of a distal end of the embodiment of the suturing device of FIG. 4A.
Figure 9:
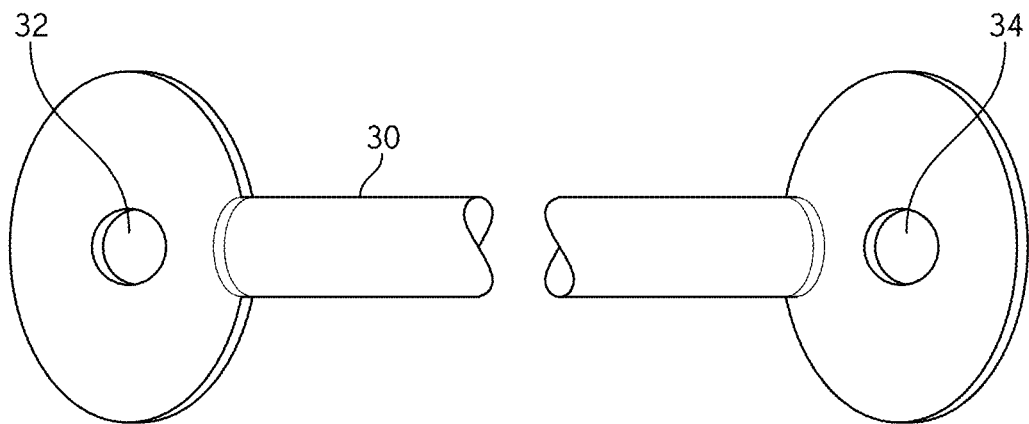
FIG. 9 illustrates an embodiment of a suture strand configured for use with a suturing device according to one embodiment.
Figure 10A:
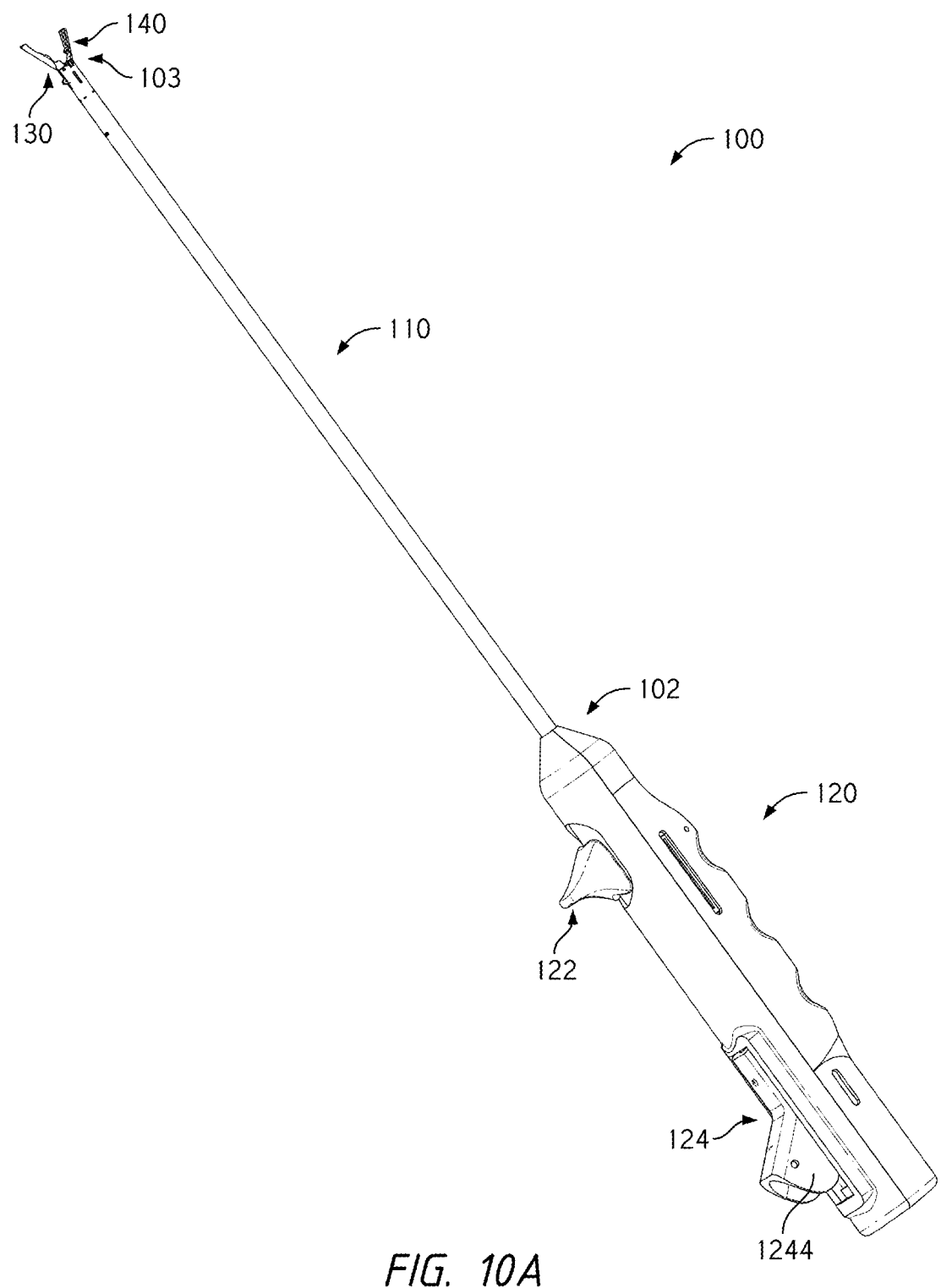
FIG. 10A illustrates a perspective view of an embodiment of a suturing device in an open configuration.
Figure 10B:
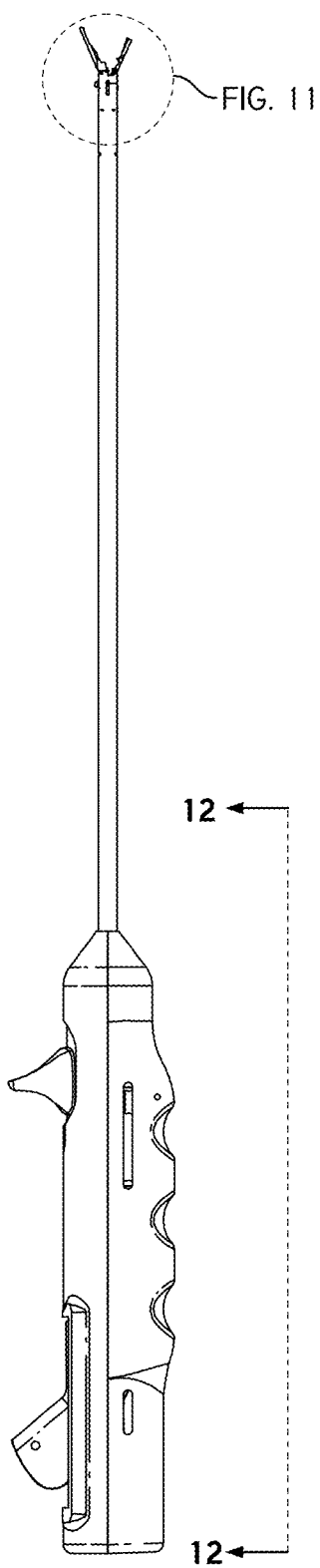
FIG. 10B illustrates a side view of the embodiment of the suturing device of FIG. 10A.

The first and second tissue grasping arms 130, 140 can each have an elongate shape extending distally from the distal end 103 of the elongate housing 100. As shown in FIGS. 4A-4B and 5, the first and second tissue grasping arms 130, 140 can have a closed configuration when the first and second tissue grasping arms 130, 140 are generally parallel with each other, and also generally parallel with the longitudinal axis of the elongate housing 100. As shown in FIGS. 9A-9B and 10, the first and second tissue grasping arms 130, 140 can have an open configuration when distal tips of the first and second tissue grasping arms 130, 140 move away from each other and from the longitudinal axis of the elongate housing 100.

The first and second tissue grasping arms 130, 140 can have identical or substantially shape and/or dimension so that they can be generally mirror-images about the longitudinal axis of the elongate housing 110. The first and second tissue grasping arms 130, 140 can have different shapes and dimensions as shown in FIGS. 4A to 14D. As shown in FIGS. 6A-6B and 7B-7C, the first and second tissue grasping arms 130, 140 can have tissue facing surfaces 136, 146. A portion of the tissue facing surfaces 136 and 146 can have complementary slanted surfaces. The slanted surfaces can provide a horizontal force component when the first and second tissue grasping arms 130, 140 are in a closed configuration, and can have a better grip on the tissues. Additional complementary grooves and protrusions, such as a groove 135 and a protrusion 145, can also contribute to a better grip on the tissues. One arm can be longer than the other arm. As shown in the illustrated embodiment, the first tissue grasping arm 130 can be longer than the second tissue grasping arm 140, which can facilitate gripping the leaflets together. As shown in FIGS. 7A and 7C, the second tissue grasping arm 140 can terminate distally in two tines 140A, 140B with a gap between the two tines 140A, 140B. The gap can provide room for tissue the first and second tissue grasping arms 130, 140 moves to the closed configuration to grasp the tissue between the arms.

Figure 6A:
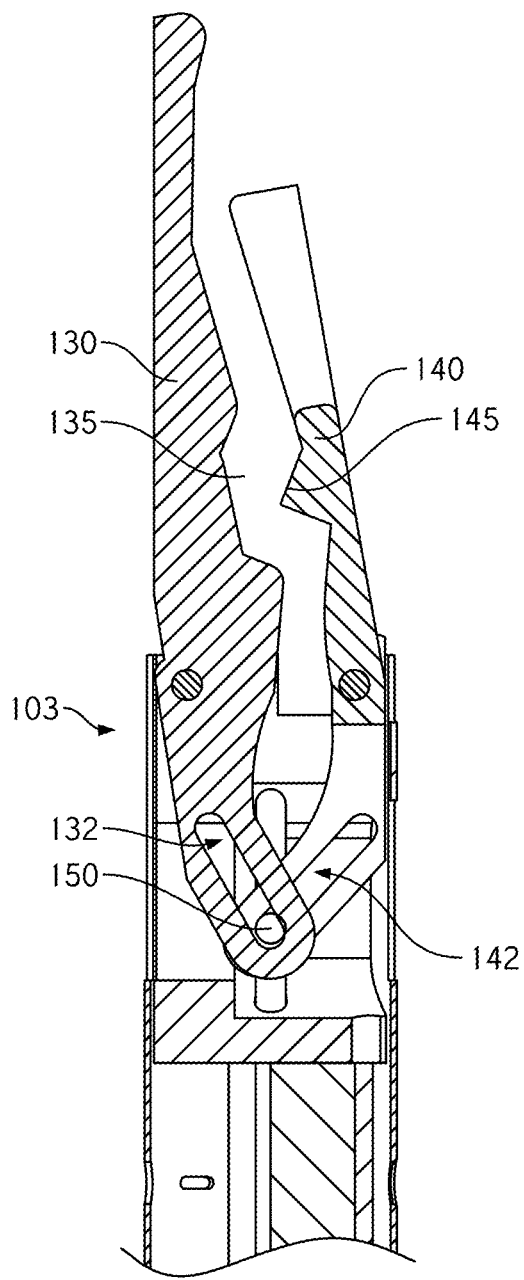
FIG. 6A illustrates a cross-sectional view of a distal end of the embodiment of the suturing device of FIG. 5.
Figure 6B:
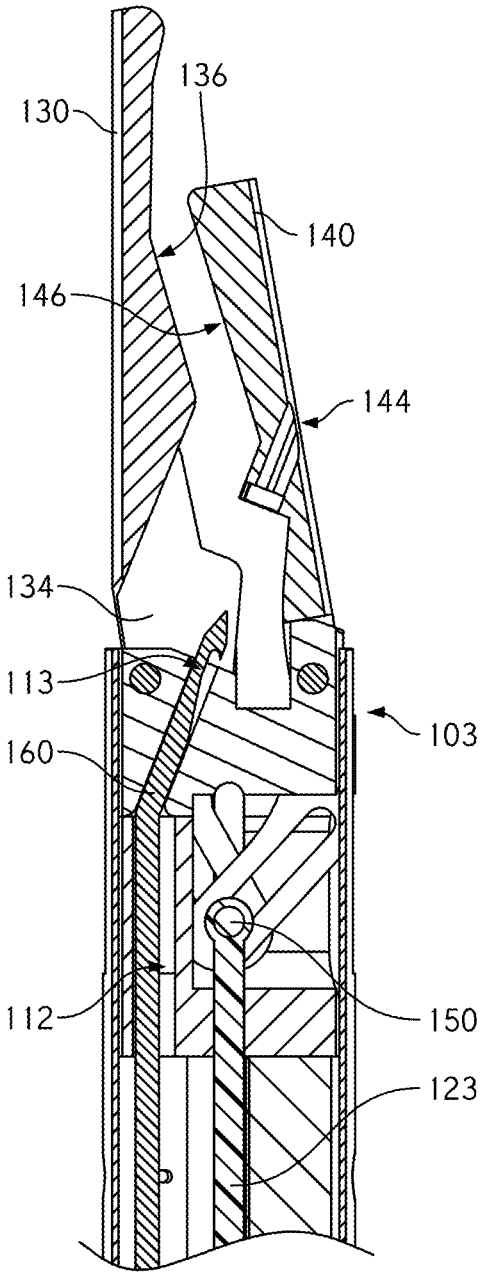
FIG. 6B illustrates another cross-sectional view of a distal end of the embodiment of the suturing device of FIG. 5 at a plane that is offset from the central plane as shown in FIG. 6A and illustrates a cross-sectional view of a needle guide track and a needle.
Figure 7A:
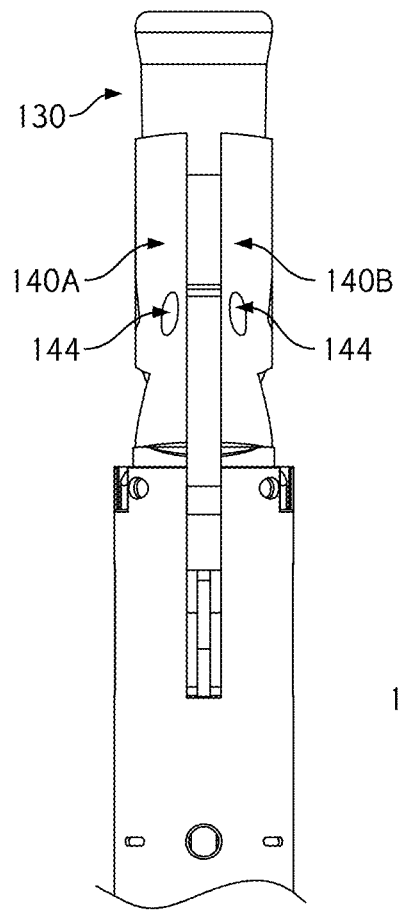
FIG. 7A illustrates an enlarged front view of a distal end of the embodiment of the suturing device of FIG. 4A.

As shown in FIGS. 6A-6B, the first and second tissue grasping arms 130, 140 can be connected at their proximal ends. The connection can be located proximal to the distal end 103 of the elongate housing 100 when the first and second tissue grasping arms 130, 140 are in the closed configuration. Specifically, each of the first and second tissue grasping arms 130, 140 can include an elongate slot 132, 142 at an angle from the longitudinal axis of the elongate housing 100. Distal ends of the elongate slots 132, 142 can overlap to allow a cross pin 150 to pass through both the elongate slots 132, 142. The open and closed configurations described above can be pivoted at the cross pin 150. As will be explained in more details below, the handle 120 can have one or more actuators for opening and closing the first and second tissue grasping arms 130, 140. The cross pin 150 can be advanced distally to open the first and second tissue grasping arms 130, 140. The cross pin 150 can be pulled proximally to close the first and second tissue grasping arms 130, 140.

Figure 7B:
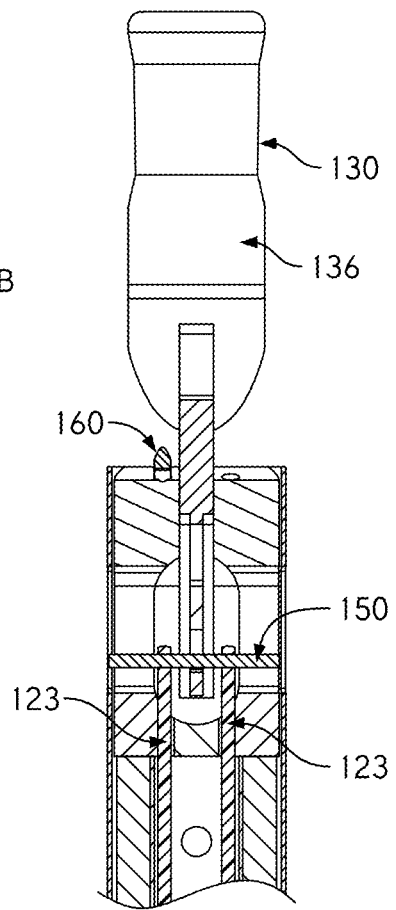
FIG. 7B illustrates a cross-sectional view of a distal end of the embodiment of the suturing device of FIG. 7A looking into the plane of FIG. 7A with a second tissue grasping arm removed.
Figure 7C:
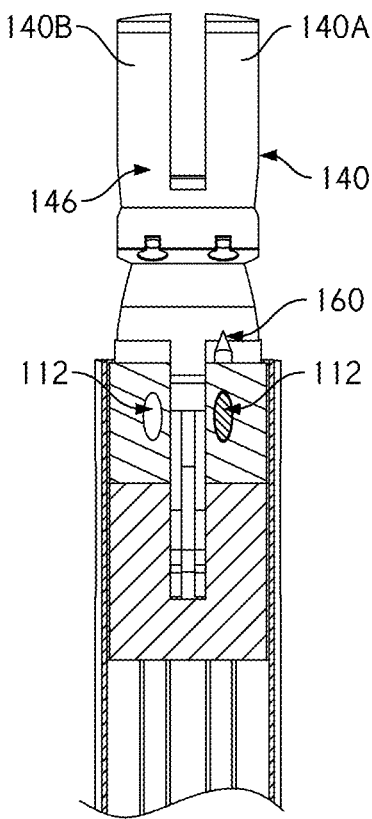
FIG. 7C illustrates an enlarged cross-sectional view of a distal end of the embodiment of the suturing device of FIG. 4A looking out of the plane of FIG. 7B with a first tissue grasping arm removed.

As further shown in FIG. 6B, which shows a cross-section of the tissue-engaging assembly at a plane offset from a central plane as shown in FIG. 6A, the second tissue grasping arm 140 can include at least one suture mount 144. As illustrated in FIGS. 7A and 7C, the second tissue grasping arm 140 can include two suture mounts 144. The two suture mounts 144 can be generally symmetrical about a central vertical axis of the second tissue grasping arm 140. The second tissue grasping arm 140 can include more than two suture mounts 144. The suture mount 144 can include one lumen (FIG. 6B) to allow movement of a suture catcher, such as a needle 160 or a hook, through the suture mount 144. The needles 160 can be housed inside needle lumens 112 of the suturing device 100. Each needle lumen 112 can house one needle 160. As shown in FIGS. 7A-7C, the suturing device 110 can include two needle lumens 112. (In FIGS. 7B and 7C, one needle is omitted from one of the needle lumens 112 for clarity.) The needle lumens 112 can be located substantially symmetrically about the longitudinal axis of the elongate housing 110. A plane encompassing openings of the two needle lumens 112 can be substantially parallel to a plane encompassing openings of the two suture mounts 144 on the tissue facing surface 146. The needle lumens 112 can be inside the elongate housing 110, or in a separate catheter running alongside the elongate housing 110. As shown in FIG. 6B, the needle lumens can be on an opposite side of the elongate housing 100 from the second tissue grasping arm 140. The needle lumens can be diametrically opposite the second tissue grasping arm 140.

Each of the suture mounts 144 can further be configured to releasably hold a suture portion. FIG. 9 illustrates an example suture strand 30 having a hole or an eyelet 32, 34 that can be formed at each end of a single suture strand 30. The eyelet 32, 34 can be configured to allow a hook or needle through an opening of the eyelet in a suturing procedure. After the needle 160 has engaged the eyelet of the suture portion, the needle 160 can be retracted through the same lumen. The retraction of the needle 160 can thereby pull the suture strand 30 through the lumen and also through layers of tissue grasped by the first and second tissue grasping arms 130, 140. The suture portion held at each of the suture mounts 144 can comprise a single suture strand. As described above with reference to FIG. 3, the eyelet 32, 34 at each end of the single suture strand 30 can be passed through one of the lumens of the suture mounts 144 on the second tissue grasping arm 140, and be pulled through the two leaflets that are grasped by the first and second tissue grasping arms 130, 140. Additional details about the example suture strand 30 are provided in U.S. patent application Ser. No. 11/503,652, entitled "SUTURING DEVICE AND METHOD" and filed on Aug. 14, 2006, now U.S. Pat. No. 8,348,962, which is incorporated herein by reference in its entirety.

Figure 15A:
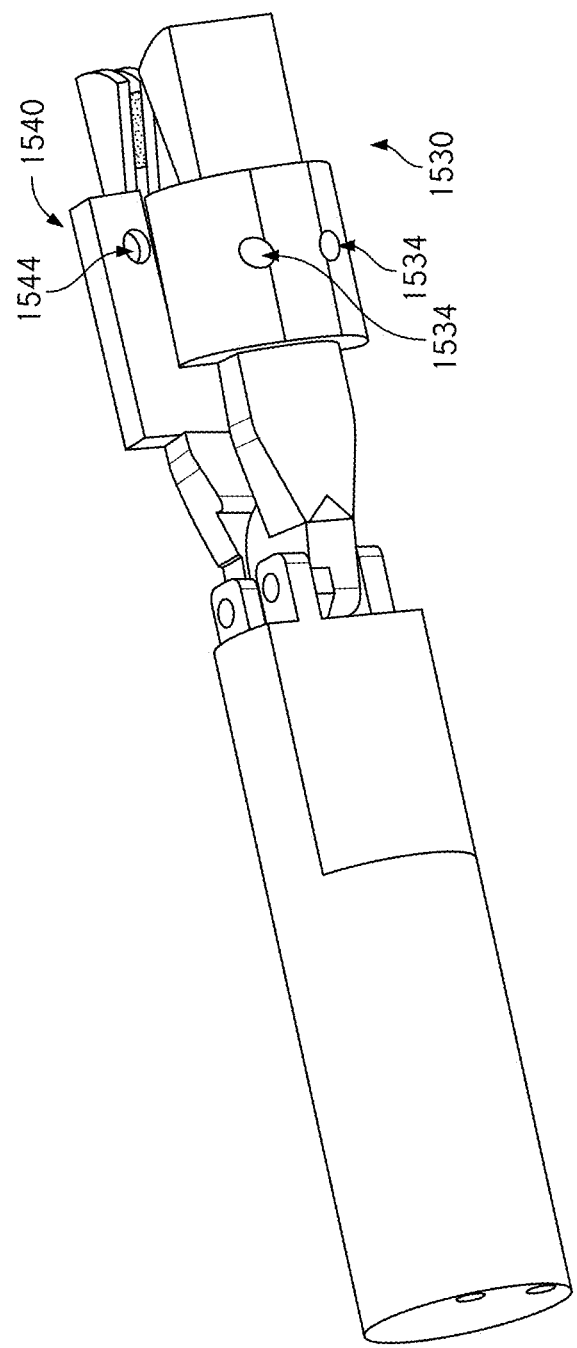
FIGS. 15A-15B illustrate an embodiment of a distal end of a suturing device.
Figure 15B:
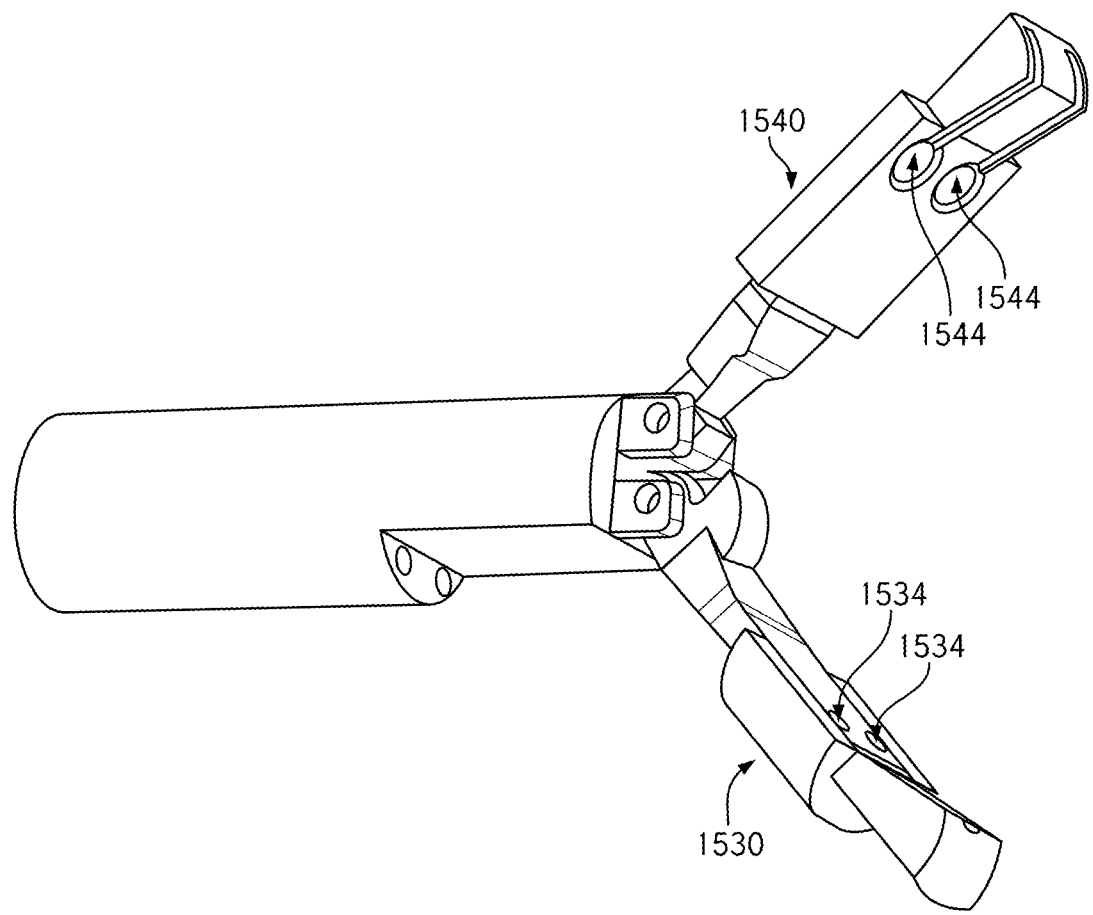

As shown in FIG. 6B, the needle lumens 112 can have openings located on the same side of the longitudinal axis of the elongate housing 110 as the first tissue grasping arms 130 and on the opposite side of the longitudinal axis of the elongate housing 110 as the second tissue grasping arms 140. The first tissue grasping arm 130 can be dimensioned so that the needles 160 can be passed unhindered from the distal end 103 of the elongate housing 110 to the suture mount 144 on the second tissue grasping arm 140. As shown in FIGS. 5 and 6B, the first tissue grasping arm 130 can have one or more cut-out portions 134, such as from left and right edges of the first tissue grasping arm 130 to provide a clear path for the needles 160. The needle lumens can have openings on the distal end 103 of the elongate housing 110 such that the needles' trajectories may not intersect the first grasping arm 130. FIGS. 15A-15B illustrate a first tissue grasping arm 1530 that can include two lumens 1534. As shown in FIG. 15B, the needle lumens 1512 can have openings located on the same side of the longitudinal axis of the elongate housing 1510 as the first tissue grasping arms 1530 and on the opposite side of the longitudinal axis of the elongate housing 1510 as the second tissue grasping arms 1540. The lumens 1534 can be located along trajectories of the needles so that needles can be deployed into suture mounts 1544 on a second tissue grasping arm 1540 through the lumens 1534.

Turning back to FIGS. 4A-4B, the handle 120 can have an elongate handle housing 128 generally extending along a longitudinal axis of the elongate housing 110. The handle 120 can be of different shapes. The handle can include actuators, such as a slide 122 and a switch 124. As shown in FIGS. 4A-4B, the slide 122 can be distal of the switch 124. Other arrangements of the slide 122 and the switch 124 can also be used based on the disclosure herein.

Figure 8:
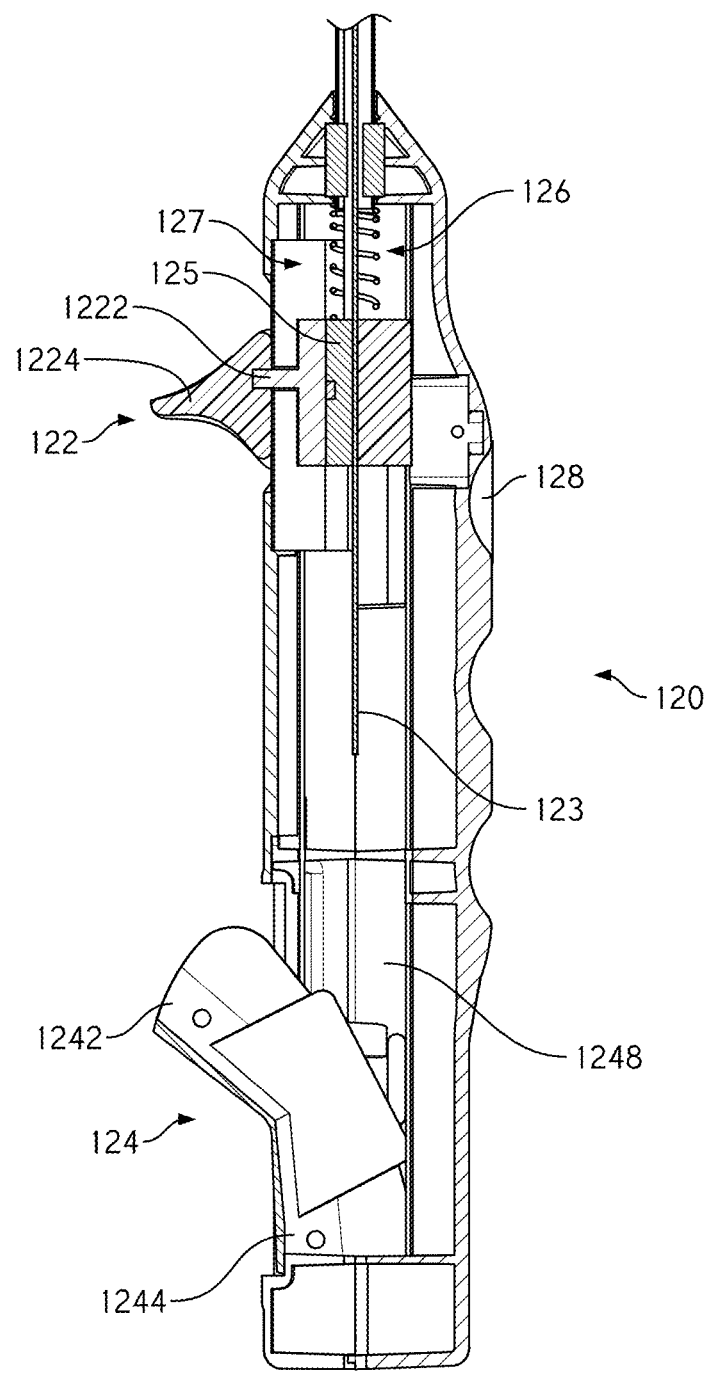
FIG. 8 illustrates an enlarged cross-sectional view of a proximal end of the embodiment of suturing device of FIG. 4A.
Figure 12:
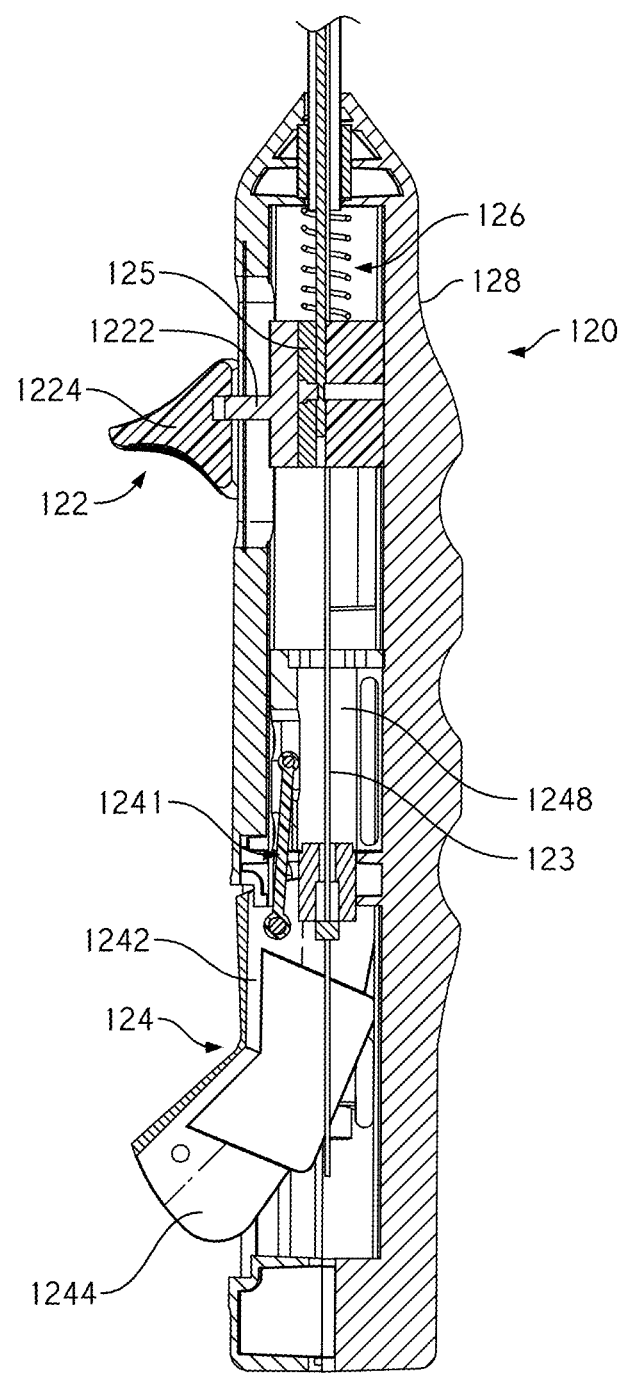
FIG. 12 illustrates an enlarged cross-sectional view of a proximal end of the embodiment of the suturing device of FIG. 10A.

As shown in FIGS. 8 and 12, the slide 122 can be configured to deploy and retract the needles 160. The slide can have a handle portion 1222 and a user portion 1224. The handle portion 1222 can be located within the handle housing 128. The user portion 1224 can protrude outward from the handle housing 128. The user portion 1224 can be shaped to allow a user to move the slide 122 with a thumb. The user portion 1224 and the handle portion 1222 can be connected such that the user and handle portions 1224, 1222 move in unison when a user moves the user portion 1224. The handle 120 can include a gap 127 that is longer than a length of the handle portion 1222 of the slide 122 along the longitudinal axis of the elongate housing 110. The relative lengths and positions of the gap 127 and the handle portion 12224 can limit the range of axial movement of the slide 122, which can in turn limit the range of movement of the needle 160. The relative lengths and positions of the gap 127 and the handle portion 12224 can allow the needle 160 to travel a sufficient distance to engage the suture portion on the suture mount 144, but can prevent the needle tip from pinching into anatomical structures surrounding the valve. The limited range of movement of the needle 160 can therefore prevent injury of the patient's body tissue by the needle when the suturing device 100 is in use.

The handle portion 1222 can be fixedly attached to a needle deployment rod 125 (shown in FIGS. 8, 11, and 13A-13C). The needle deployment rod 125 can span substantially a length of the elongate housing 110 and a distal portion of the handle 120 along its length. As shown in FIG. 6B, the needle deployment rod 125 can be coupled to the needles 160 at or near the distal end 103 of the elongate housing 110. A distal spring 126 can be located between a distal surface of the handle portion 1222 of the slide 122 and a distal inner surface of the handle housing 128. The distal spring 126 can bias the slide 122 in a proximal direction such that the needles 160 can be in a retracted position. When a user pushes the slide 122 distally, which can compress the distal spring 126, the needles 160 can be deployed via the needle lumens 112 inside the elongate housing.

Figure 11:
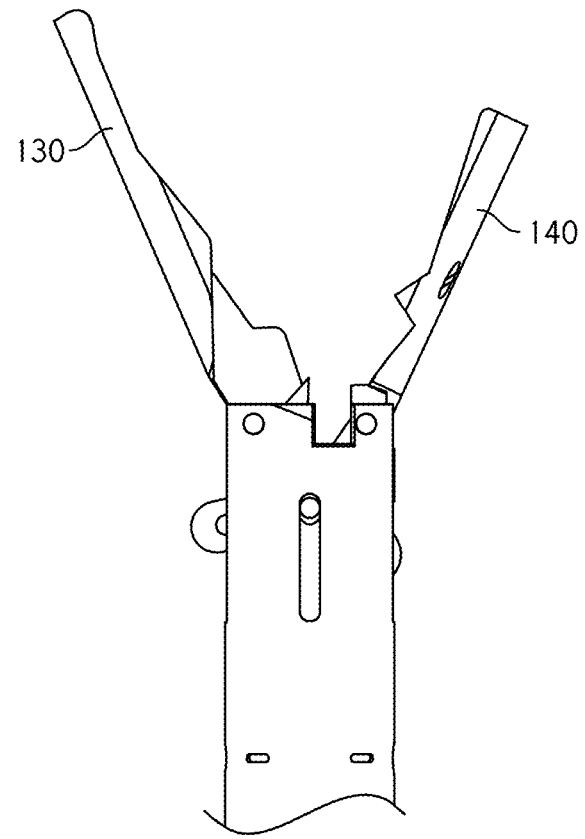
FIG. 11 illustrates an enlarged side view of a distal end of the embodiment of the suturing device of FIG. 10A.

The switch 124 can be configured to open and close the first and second tissue grasping arms 130, 140. Turning to FIGS. 8 and 11, the switch 122 can include an distal portion 1242 and a proximal portion 1244. The distal portion 1242 and the proximal portion 1244 can form an angle and be pivoted at the joint of the distal portion 1242 and the proximal portion 1244 in a seesaw type of configuration. When the distal portion 1242 is pressed into the handle housing 128, the proximal portion 1244 protrudes outward from the handle housing 128, and vice versa.

As shown in FIGS. 8 and 12 (and also FIGS. 13A-13D), the distal portion 1242 can be adjacent to a sliding block 1248. The distal portion 1242 can be connected to the sliding block 1248 via a linkage bar 1241. The sliding block 1248 can thus move axially along the longitudinal axis of the elongate housing 100 by the seesaw motion of the switch 124. The sliding block 1248 can be connected to two cables or thin rods 123. The cables or thin rods 123 can span substantially the length of the elongate housing 110 and a substantially portion of the length of the handle 120. As shown in FIG. 7B, the cables or thin rods 123 can be hingedly attached to the cross pin 150. A user can switch between opening and closing the first and second tissue grasping arms 130, 140 by pressing on the distal or proximal portions 1242, 1244 of the switch 124, which can be configured to cause axial movement of the sliding block 1248, the cables 123, and the cross pin 150.

As shown in FIG. 8 (also in FIG. 13B), the proximal portion 1244 can be pressed to cause the first and second tissue grasping arms 130, 140 to be in a closed configuration. In the closed configuration, the sliding block 1248 can be pushed proximally, thereby pulling the cross pin 150 proximally to close the arms. As shown in FIG. 12 (also in FIG.

13A), the distal portion 1242 can be pressed to cause the first and second tissue grasping arms 130, 140 to be in an open configuration. In the open configuration, the sliding block 1248 can be pushed distally, thereby pushing the cross pin 150 distally to open the arms. Having a pair of cables or thin rods positioned substantially symmetrically about the longitudinal axis of the elongate housing 110 can more evenly distribute an axial force when opening or closing the tissue grasping arms.

Figure 13A:
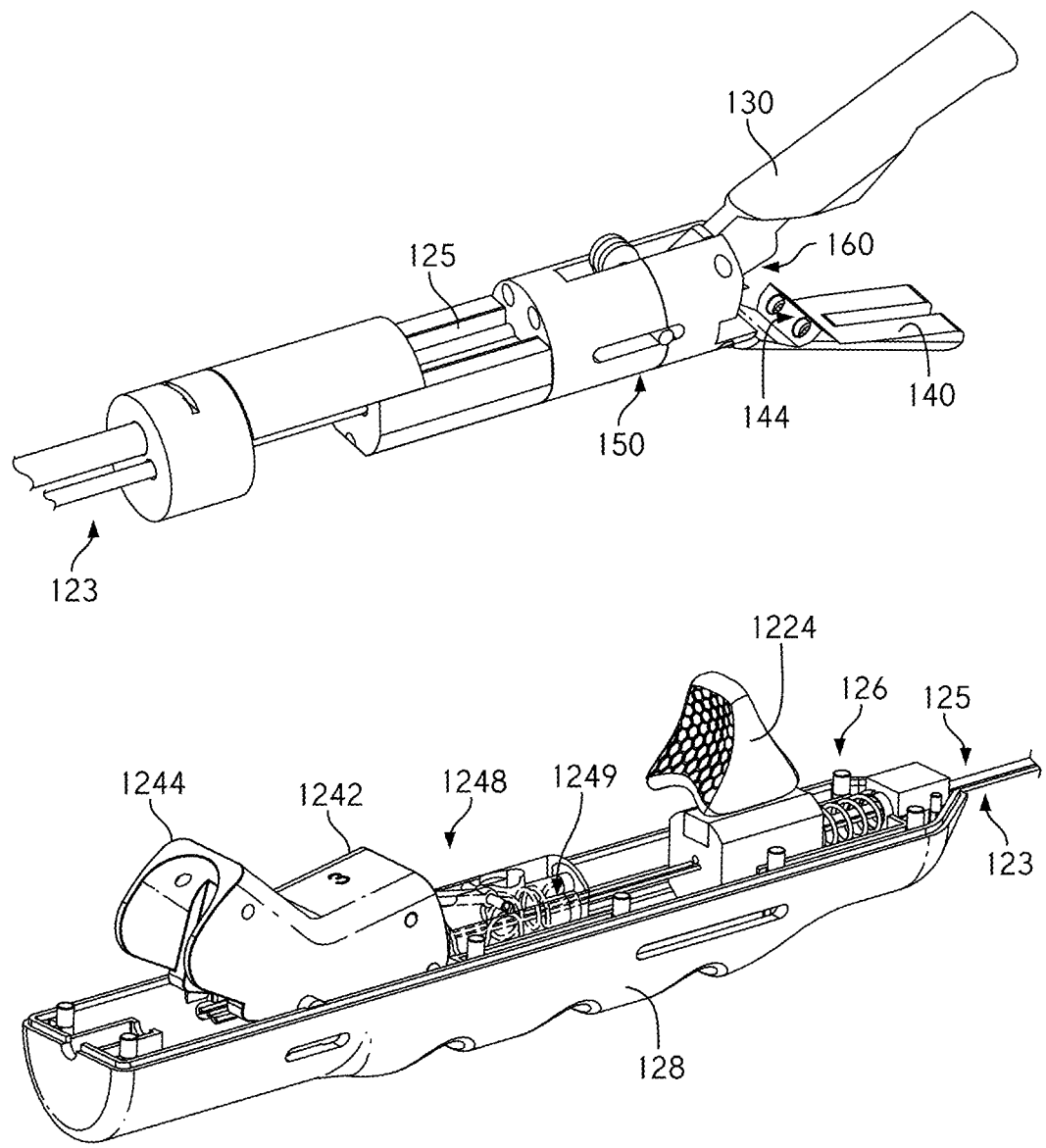
FIGS. 13A-13D illustrate various configurations of an embodiment of a suturing device with an upper portion of a handle housing and an elongate housing removed for clarity.

Additional details of the operations of the slide 124 and the switch 122 will now be explained with reference to FIGS. 13A-13D, which are shown with the elongate housing 110 and an distal portion of the handle housing 128 removed for clarity. In each of FIGS. 13A to 13D, the suturing device 100 is shown with the tissue grasping arms in the top figure and the handle in the bottom figure. In FIG. 13A, the needles 160 are in a retracted position and the handle portion 1222 of the slide 122 can be biased proximally. The distal portion 1242 of the switch 124 is pressed down so that the distal portion 1242 can be generally parallel to the longitudinal axis of the elongate housing 110. An end surface of the distal portion 1242 abuts a proximally facing surface of the sliding block 1248 to push the sliding block 1248 distally so as to open the first and second tissue grasping arms 130, 140. The sliding block 1248 can comprise or encase a proximal spring 1249. The proximal spring 1249 can be biased proximally and the end surface of the distal portion 1242 of the switch 124 compresses the proximal spring 1249 in order to push the sliding block 1248 distally.

Figure 13B:
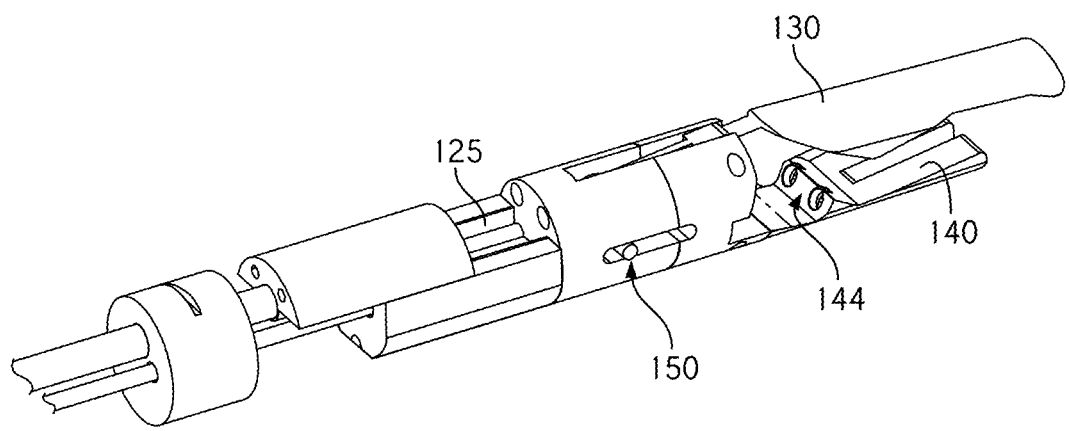
Figure 13B:
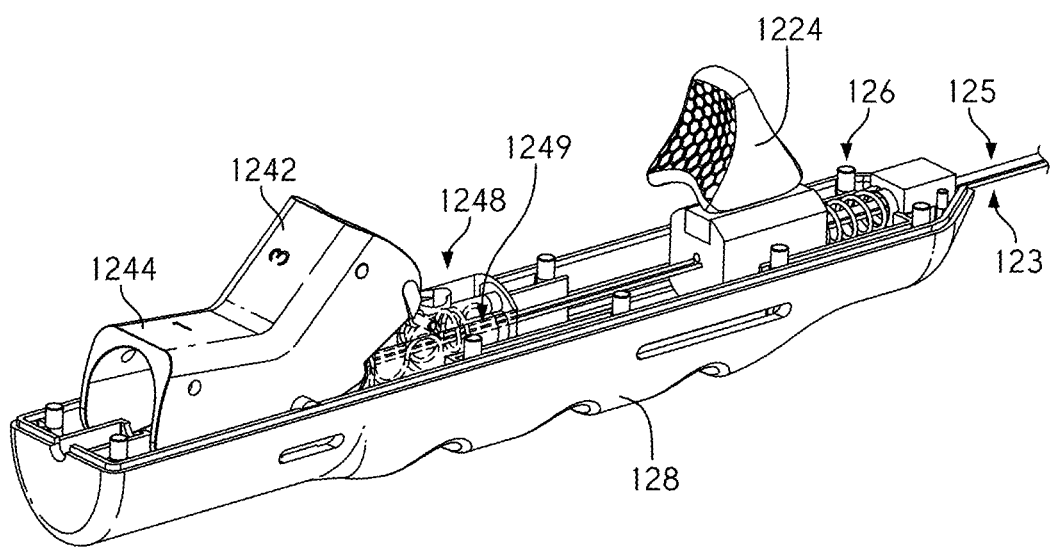

In FIG. 13B, the needles 160 are still in a retracted position. The user has partially pressed down the proximal portion 1244 so that neither the distal portion 1242 nor the proximal portion 1244 of the switch 124 is completely pressed down. Each of the distal portion 1242 and the proximal portion 1244 of the switch 124 can form an angle with the longitudinal axis of the elongate housing. The end surface of the distal portion 1242 is no longer abutting the proximally facing surface of the sliding block 1248. The proximal spring 1249 regains a portion of its free length and moves the sliding block 1248 proximally. This movement can cause the first and second tissue grasping arms 130, 140 to move to a closed configuration.

Figure 13C:
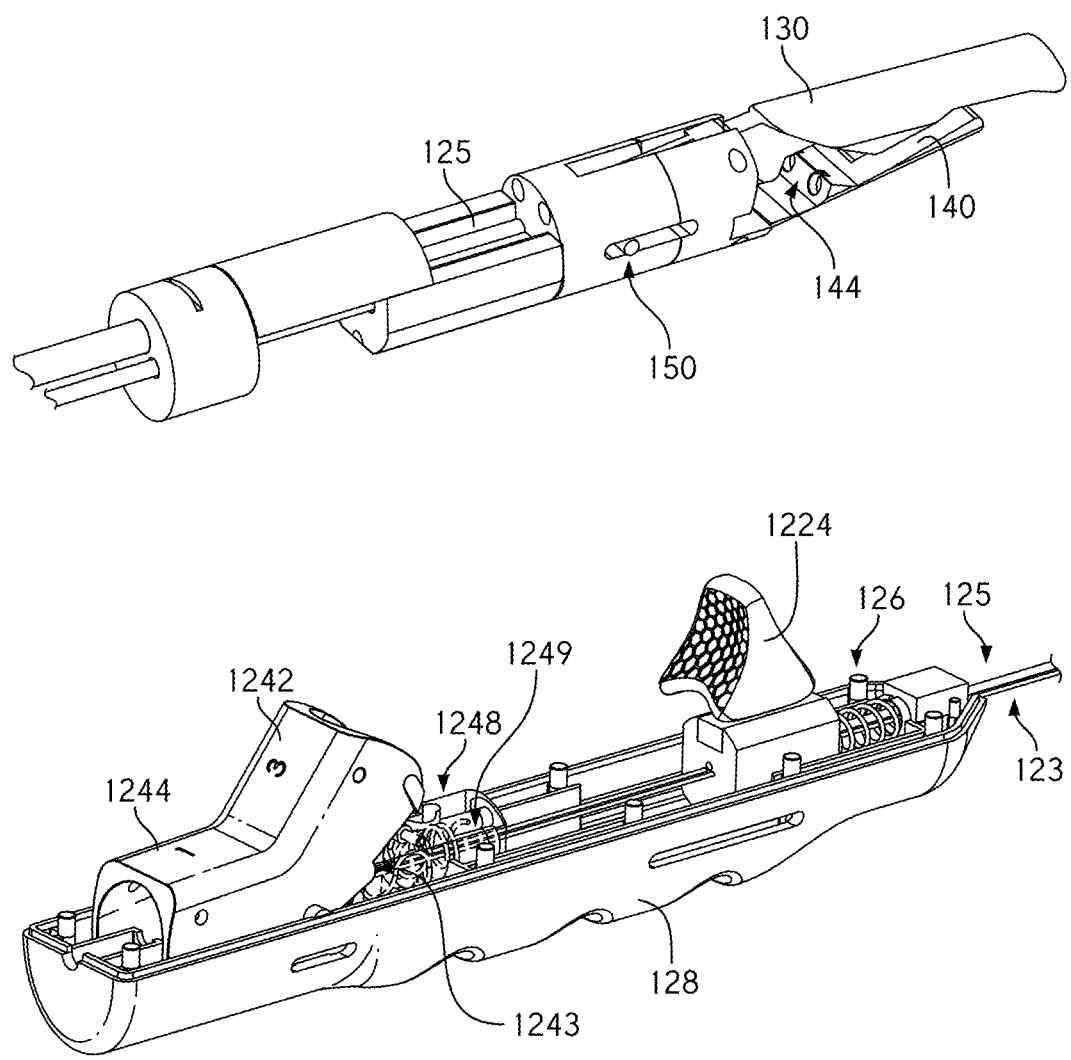

FIG. 13C illustrates an optional "grip" configuration of the first and second tissue grasping arms 130, 140. The needles 160 are still in a retracted position. The proximal portion 1242 of the switch 124 is pressed down completely by the user so that the proximal portion 1242 can be generally parallel to the longitudinal axis of the elongate housing 110. The sliding block 1248 is pulled further proximally due to the movement of the switch 124 until the proximally facing surface of the sliding block 1248 abuts a ridge 1243 of the distal portion 1242. The additional proximal movement of the sliding block 1248 can close the first and second tissue grasping arms 130, 140 even further compared to when the arms are in the closed configuration. A distance between the first and second tissue grasping arms 130, 140 can be smaller in this "grip" configuration than the distance when the first and second tissue grasping arms 130, 140 are in the closed configuration. The first and second tissue grasping arms 130, 140 can thus form a tighter grip on the tissue between the arms. The proximal spring 1248 further biases the sliding block 1248 proximally, which can help maintain a firm grip by the first and second tissue grasping arms 130, 140 in this configuration. The suturing device 100 can be further configured such that the slide 122 cannot move, and the needles 160 cannot be deployed, except when the first and second tissue grasping arms 130, 140 are in the "grip" configuration. For example, the user completely pressing down the proximal portion 1244 of the switch can release a stopper that prevents the slider 122 from move proximally. This can prevent accidental deployment of the needles 160, and increase safety of the suturing device 100.

Figure 13D:
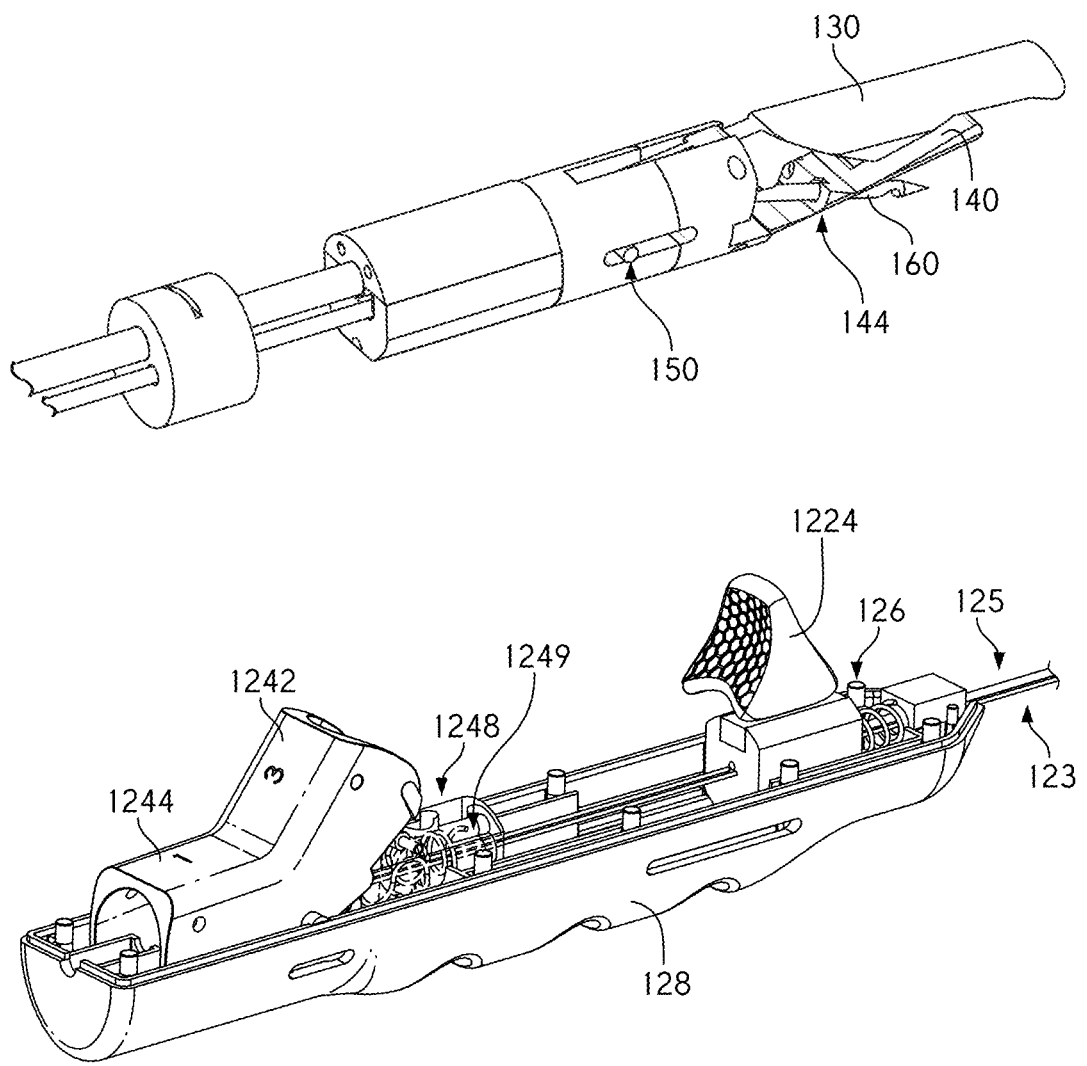

In FIG. 13D, while the first and second tissue grasping arms 130, 140 are in the closed or the optional "grip" configuration, the needles 160 are deployed by moving the handle portion 1222 of the slide 122 distally against the distal spring 126. Although not shown, the user can either move the slide 122 proximally or let go of the slide 122 to retract the needles.

The actuators can be different types of actuators suitable for use with the suturing device 100 disclosed herein. For example, instead of the slide 122, a push button can be used to compress the spring 126. The user can continue pressing down on the push button such that the pressing down can initially deploy the needles and subsequently retract the needles without the need for a separate action from the user for needle retraction.

Although the suturing device 100 described above can transition between the open and closed configuration by moving both the first and second tissue grasping arms 130, 140, a suturing device of the present disclosure can have one fixed tissue grasping arm and one rotatable tissue grasping arm.

Suturing Device with More than Two Tissue Grasping Arms

Figure 15C:
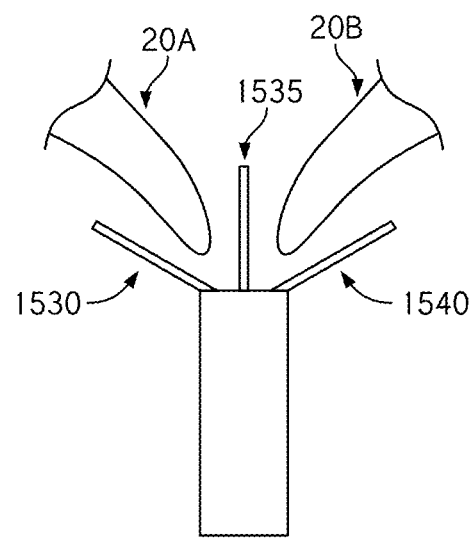
FIGS. 15C-15L illustrate schematically additional embodiments of tissue grasping arms of a suturing device.

Turning to FIGS. 15C-15L, embodiments of suturing devices of the present disclosure can include more than two tissue grasping arms. As shown in FIG. 15C, the suturing device can have a first side tissue grasping arm 1530, a second side tissue grasping arm 1540, and a central tissue grasping arm 1535. The central tissue grasping arm 1535 can be fixed or movable. The first and second side tissue grasping arms 1530, 1540 can each cooperate with the central tissue grasping arm 1535 to grasp one leaflet. In a closed configuration, the two leaflets 20A, 20B can be brought together with the central tissue grasping arm 1535 between the two leaflets 20A, 20B.

Figure 15D:
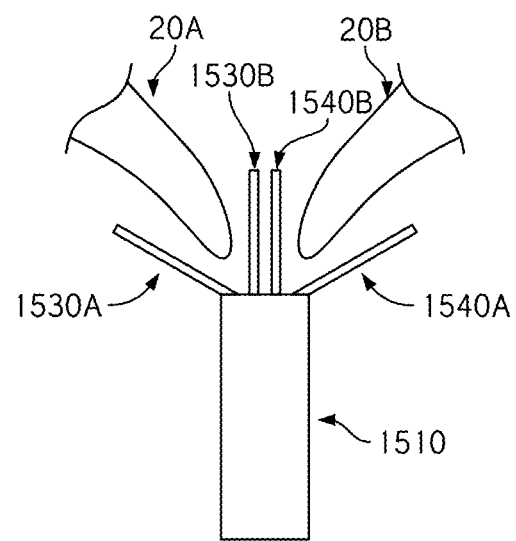

As shown in FIG. 15D, the suturing device can have a first pair of tissue grasping arms 1530A, 1530B, and a second pair of tissue grasping arms 1540A, 1540B. The arms 1530A, 1540A can be located on two opposite (e.g. diametrically opposite) sides of the longitudinal axis of the elongate shaft 1510. The arms 1530B, 1540B can be located between the arms 1530A, 1540A and on two sides of the longitudinal axis. The first and second pairs of tissue grasping arms 1530A, 1503B, 1540A, 1540B can each grasp one leaflet. After the first and second pairs of arms 1530A, 1503B, 1540A, 1540B have each grasped one leaflet, the first and second pairs of arms 1530A, 1503B, 1540A, 1540B can be brought together toward the longitudinal axis of the suturing device to bring the two leaflets together. The first and second pairs of tissue grasping arms 1530A, 1503B, 1540A, 1540B can each have two rotatable or articulating tissue grasping arms, or one fixed or non-articulating tissue grasping arm and one rotatable or articulating tissue grasping arm.

Turning to FIGS. 15E-15L, an embodiment of the suturing device 1500 can have a first shaft 1530 and a second shaft 1540. The first and second shafts 1530, 1540 can extend distally from an elongate shaft 1510 similar to the elongate shaft 110 described above. The first shaft 1530 can include a first pair of tissue grasping arms 1530A, 1530B at its distal end. The second shaft 1540 can include a second pair of tissue grasping arms 1540A, 1540B at its distal end.

The arms 1530A, 1530B, 1540A, 1540B can have any of features of the tissue grasping arms 130, 140, 1530, 1540 described above.

The first and/or second shaft 1530, 1540 can be configured to bend di-directionally within a plane. The plane can intersect lateral sides of the first and second shafts 1530, 1540, and/or encompass a cross-section of the first and second pairs of tissue grasping arms 1530A, 1530B, 1540A, 1540B. As shown in FIG. 15H, the first and second shaft 1530, 1540 can bend by having a plurality of slits/slots/apertures 1582. The slits 1582 can each have an opening facing a lateral side of the first or second shaft 1530, 1540. The slits 1582 can be aligned on the lateral side of the first or second shaft 1530, 1540 along their respective longitudinal axes. The slits 1582 can be parallel to and/or intersect the plane intersecting the lateral sides of the first and second shafts 1530, 1540, 1540B so as to constrain bending of the first or second shaft 1530, 1540 within the plane. In some embodiments, the first and/or second shaft 1530, 1540 can bend by having a steering mechanism (e.g., using one or more pullwires), comprising flexible material(s), and/or having a pre-shaped bend. In some embodiments, the first and second shafts 1530, 1540 can have different bending features. In some embodiments, the first and second shafts 1530, 1540 can have the same bending features. In some embodiments, the slits can vary along the perimeter in order to direct bending in a particular direction or set of directions.

As shown in FIGS. 15E-15K, one of the first and/or second pairs of tissue grasping arms (e.g. the arms 1530A and 1540A) can be an articulating arm rotatable about a pivot point 1539, 1549, respectively. The other one of the first and/or second pairs of tissue grasping arms (e.g. the arms 1530B and 1540B) can be a rigid and/or non-articulating arm. In some embodiments, such as shown in FIG. 15L, both of the first and/or second pairs of tissue grasping arms can comprise articulating arms.

Figure 15E:
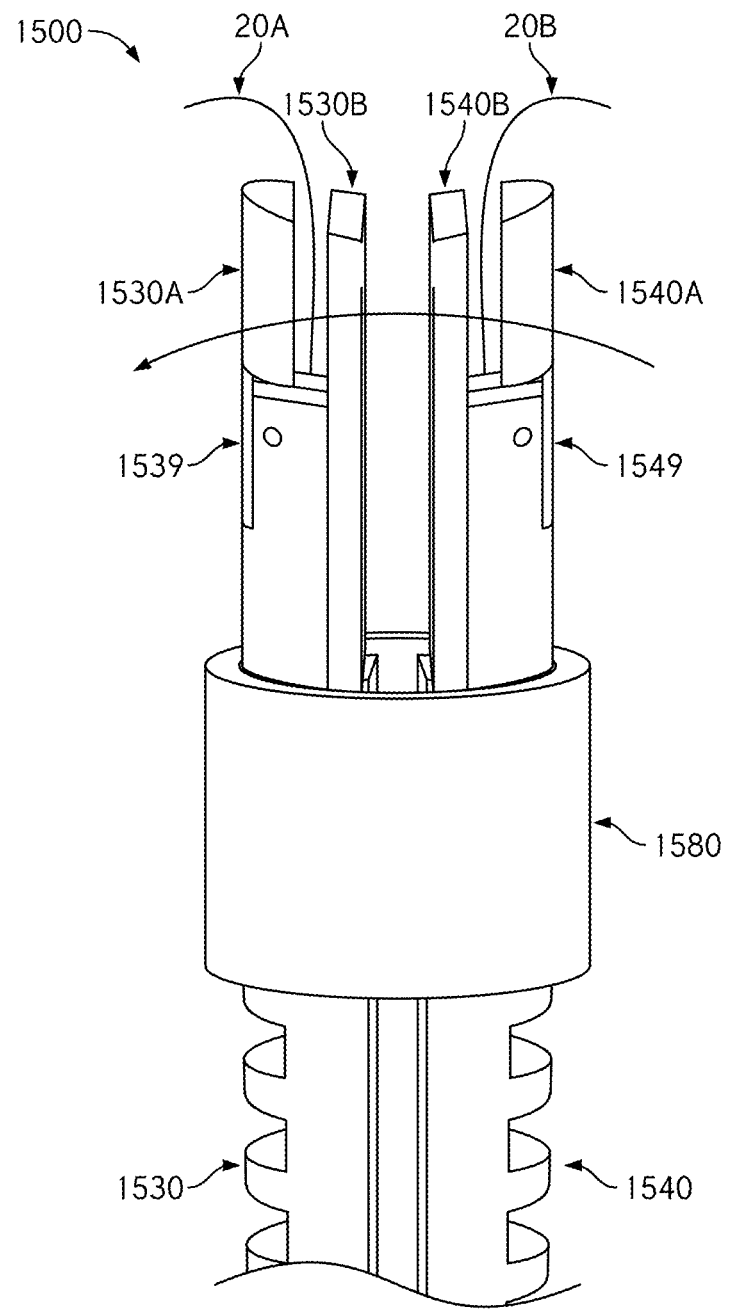
Figure 15F:
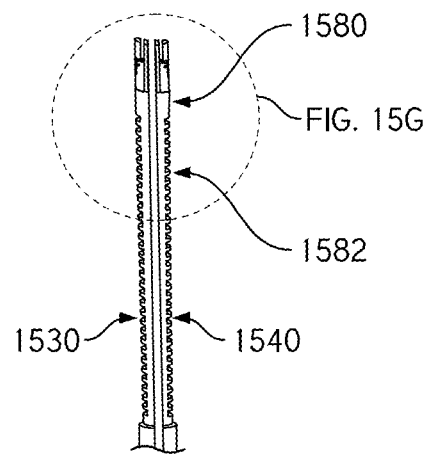
Figure 15G:
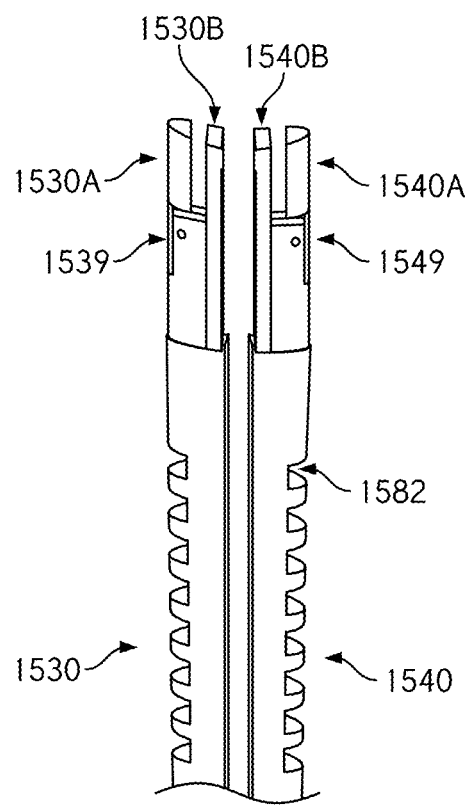
Figure 15H:
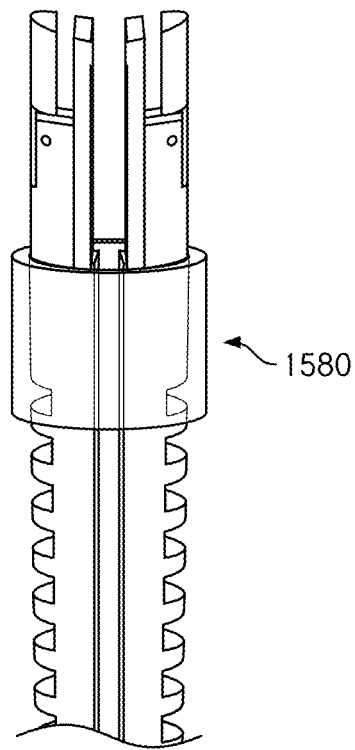
Figure 15I:
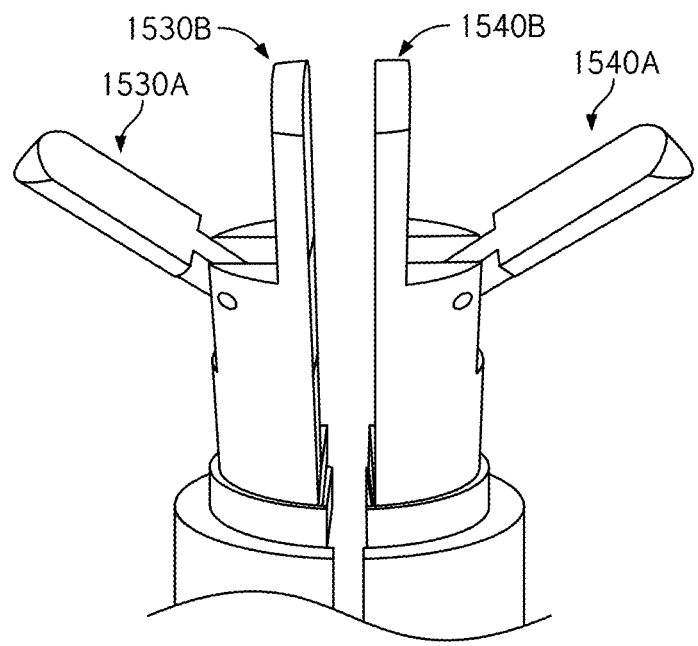
Figure 15J:
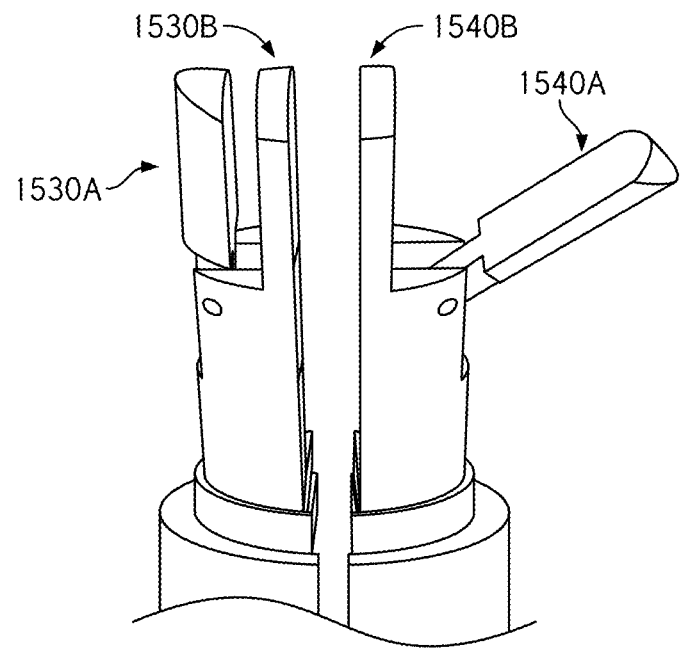
Figure 15K:
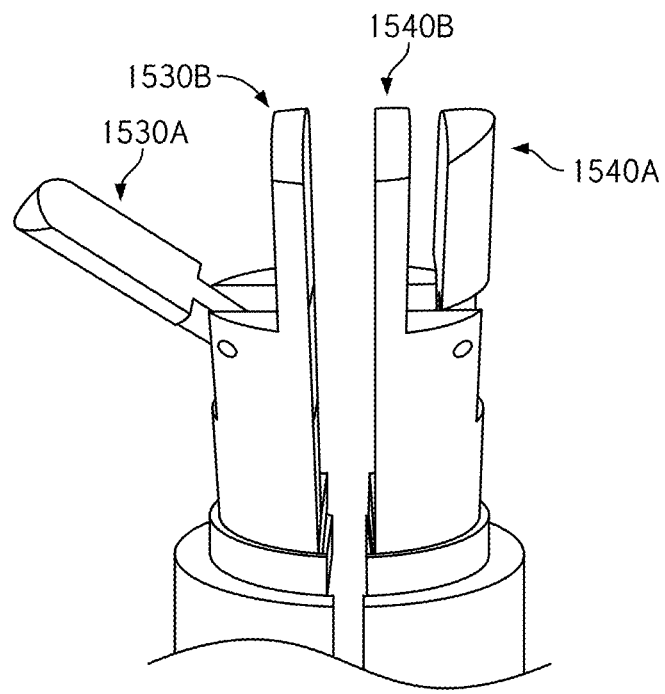
Figure 15L:
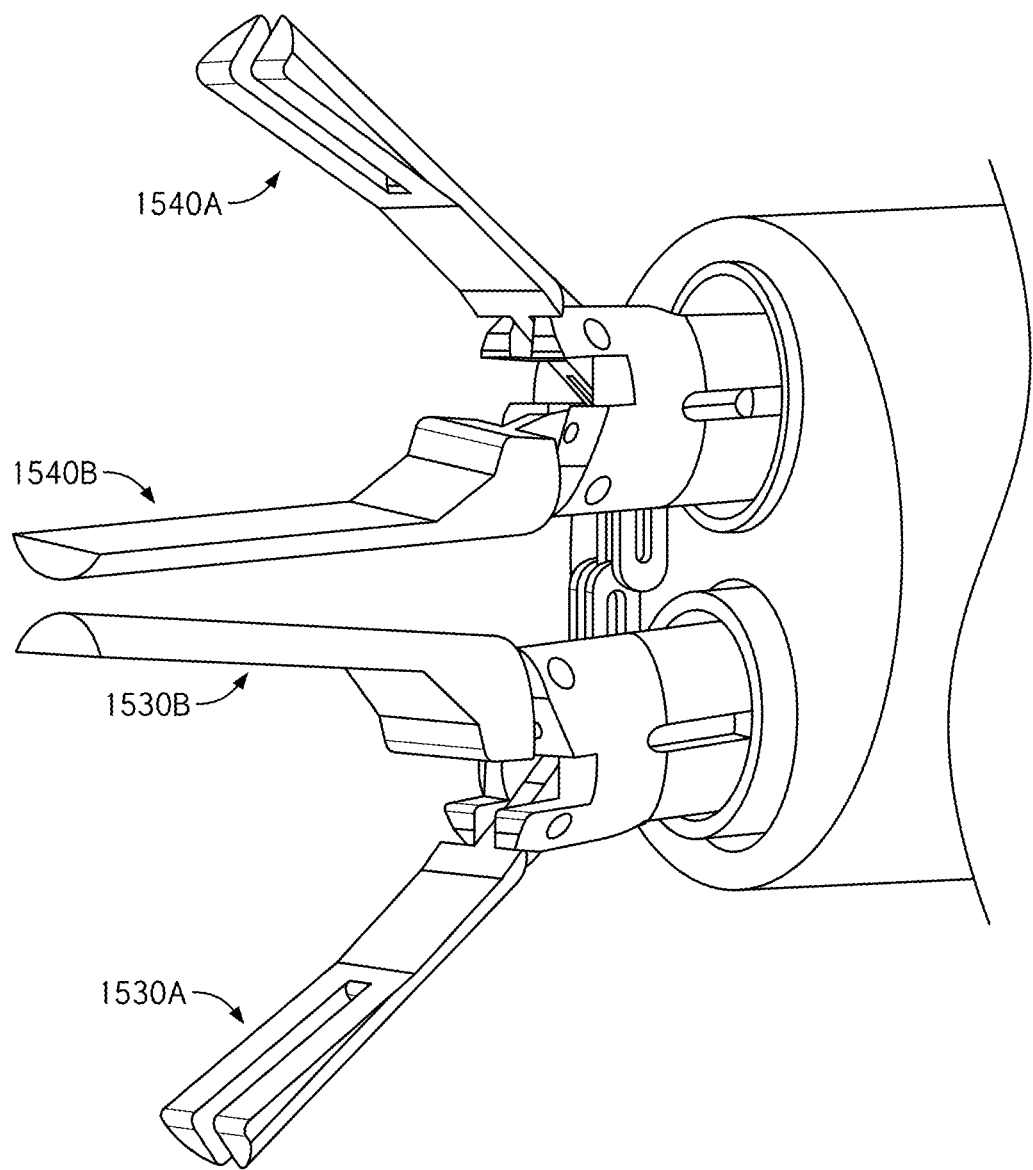

As shown in FIGS. 15I and 15L, the first and second pairs of tissue grasping arms 1530A, 1530B, 1540A, 1540B can be opened simultaneously (e.g. by rotating the arms 1530A, 1540A about the pivots 1539, 1549, respectively). As shown in FIG. 15J, the second pair of tissue grasping arms 1540A, 1540B can be opened and closed independent of the first pair of tissue grasping arms 1530A, 1530B. The second pair of tissue grasping arms 1540A, 1540B can be configured to grasp the second leaflet 20B. As shown in FIG. 15K, the first pair of tissue grasping arms 1530A, 1530B can be opened and closed independent of the second pair of tissue grasping arms 1540A, 1540B. The first pair of tissue grasping arms 1530A, 1530B can be configured to grasp the first leaflet 20A.

In some embodiments, one of the first or second pair of tissue grasping arms 1530A, 1530B, 1540A, 1540B can be retracted (e.g., moved proximally) while the other pair is being used to grasp one of the leaflets 20A, 20B (e.g., by retracting first shaft 1530 or second shaft 1540). Retracting one of the pairs of tissue grasping arms can provide more space for the remaining pair of tissue grasping arms to bend and/or have other movements in order to capture the target leaflet between the two arms.

Independent movements of the first and second pairs of tissue grasping arms 1530A, 1530B, 1540A, 1540B can allow the suturing device 1500 to extend one of the first and second pairs of arms (e.g. the arms 1530A, 1530B extending from the first shaft 1530) toward a first leaflet (e.g. the leaflet 20A) without extending the other pair of arms (e.g. the arms 1540A, 1540B extending from the second shaft 1540). The first pair of arms 1530A, 1530B can be opened and closed to grasp the first leaflet between the two arms. Further, the first pair of arms 1530A, 1530B can be steered into the particular position to best grasp the first leaflet. The suturing device 1500 can move around or reposition its distal end (e.g. by extending the second pair of arms 1540A, 1540B distally, and/or steering and/or bending the shaft 1540 coupled to the second pair of arms 1540A, 1540B) toward a second leaflet (e.g. the leaflet 20B). The suturing device 1500 can open and close the second pair of arms 1540A, 1540B to grasp the second leaflet between the two arms. The position and/or orientation of the second pair of arms 1540A, 1540B can be adjusted until the second leaflet is grasped between the two arms. In some embodiments, the suturing device 1500 can retract the first pair of arms 15030A, 1530B when grasping the second leaflet 20B using the second pair of arms 1540A, 1540B.

As shown in FIGS. 15E, 15F, and 15H, the suturing device 1500 can include a sleeve 1580 slidably disposed around the first and second shafts 1530, 1540. The sleeve 1580 can have varying lengths and thicknesses. In the illustrated embodiment, the sleeve 1580 can comprise a ring, though the particular shape of the sleeve 1580 is not limiting. The sleeve 1580 can have an internal diameter or width configured to allow the sleeve 1580 to slide proximally and distally along the first and second shafts 1530, 1540. For example, the sleeve 1580 can have two lumens, one for each of the first and second shafts 1530, 1540. As shown in FIG. 15H, the lumens can be shaped to receive the shafts 1530, 1540 so that the shafts cannot radially move in the lumens. When the sleeve 1580 is moved proximally, the first and second shafts 1530, 1540 can bend and/or move away from each other. When the sleeve 1580 is moved distally (e.g. at or near the tissue grasping arms), the sleeve 1580 can constrain and/or lock the first and second shafts 1530, 1540 close to each other. Further, moving the sleeve 1580 distally can bring the first and second shafts 1530, 1540 together, and moving the sleeve 1580 proximally can cause the first and second shaft 1530, 1540 to move apart. In some embodiments, when the sleeve 1580 is at its distalmost position, the first and second pairs of tissue grasping arms 1530A, 1530B, 1540A, 1540B can function as if they are comprised in a single unit. In some embodiments, the suturing device 1500 may not have a sleeve and the first and second shafts can be brought close together by other steering features described above. The sleeve 1580 can contain internal locking components that mate with the shafts 1530, 1540 to remain in a particular position. The sleeve 1580 can be unlocked to move proximally/distally, such as by actuation of an actuator or by applying a force that overcomes the locking component.

Bringing the first and second shafts 1530, 1540 together can bring the first and second pairs of tissue grasping arms 1530A, 1530B, 1540A, 1540B close together. The close proximity of the first and second pairs of tissue grasping arms 1530A, 1530B, 1540A, 1540B can allow one or more needles to be deployed from one pair of arms, through the other pair of arms, and engage suture portions, for example, the suture eyelets describe above, that are loaded on the other pair of arms. The one or more needles can follow a straight or curved path through the first and second pairs of tissue grasping arms 1530A, 1530B, 1540A, 1540B when the one or more needles are deployed. Thus, a single needle can be used to suture through both pairs of arms, and both leaflets held within the arms. However, in some embodiments, each pair of grasping arms can have a separate needle.

Having more than two tissue grasping arms can allow each leaflet to be captured independent of the capturing of the other leaflet. It can be easier to capture individual leaflets in sequence and bring the arms together than capturing two leaflets simultaneously and ensuring proper aligning of the leaflets.

Suturing Device with Angled Needle Guide and Method of Use

Figure 16:
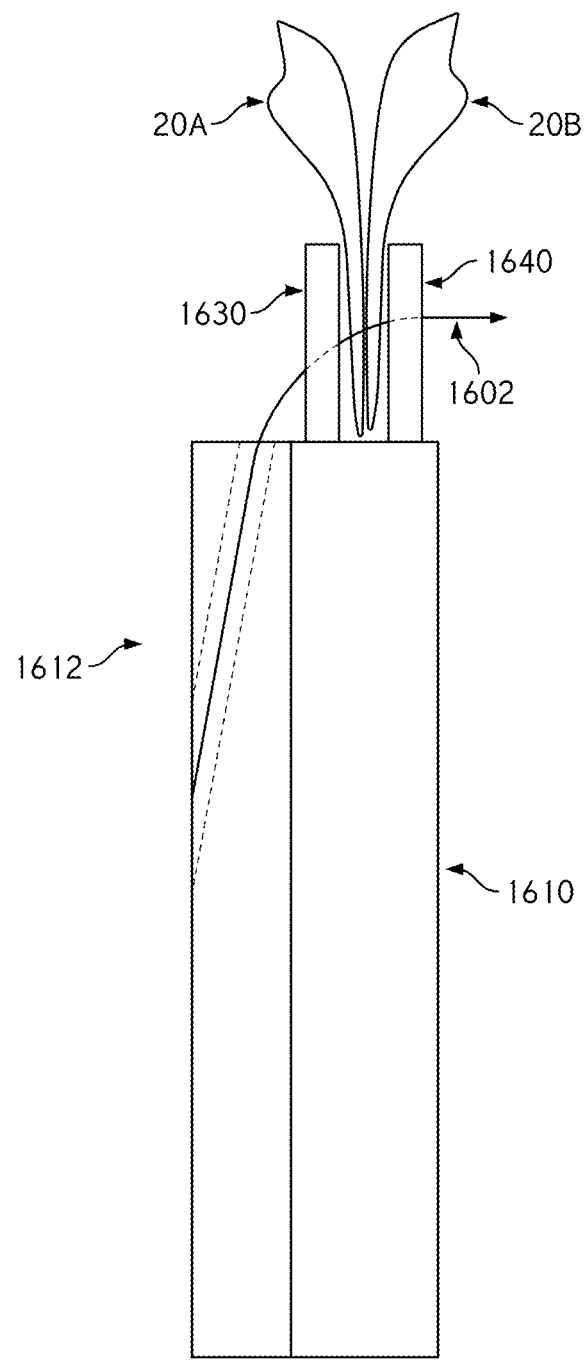
FIG. 16 illustrates schematically an example needle trajectory of the suturing device of FIG. 4A.

For the first and second tissue-grasping arms described above, the needles need to be aligned with the lumen in each of the suture mounts on the second tissue-grasping arm. FIG. 16 illustrates schematically one way for doing that. Specifically, the suturing device 1600 can have an angled needle lumen 1612. The angled needle lumen 1612 can extend toward a longitudinal axis of the suturing device 1600 in a proximal to distal direction. When the first and second tissue grasping arms 1630, 1640 have pinched the two leaflets 20A, 20B together in a closed configuration, a needle can be deployed along a curved and angled trajectory 1602 because of the angle of the needle lumen 1612. The needle can be curved and follow a curved path. The needles can also exit the lumens straight and follow a straight trajectory to the suture mounts.

The needles may not need to be deployed such that the needles pass the two leaflets perpendicularly or at substantially the same location. In the closed or optional grip configuration, the first and second tissue grasping arms can bring the leaflets next to or in close proximity with each other. Therefore, the needles can penetrate the two leaflets at similar locations, even when the needles are deployed at an angle instead of being deployed perpendicular to the tissue-grasping arms. The angled needled lumen 1612 can reduce the need of a user, such as a user, to align the needle with the suture mount on the second tissue-grasping arm, because the angled needle lumen 1612 is pre-aligned with the suture mount. This can make the suturing device easy to use. The surgical procedure can be simpler and faster. The surgical outcome can be less dependent on the skill level of the user.

The suturing device 100 can align the needles 160 using a similar technique. Turning back to FIG. 6B, the needle lumens 112 of the suturing device 100 can each have a terminal portion that can include an angled needle guide track 113. The angled needle guide track 113 can be at an angle of about 20° to about 70° with the longitudinal axis of the elongate housing 100. The angled needle guide track 113 can be at an angle of about 25° to about 45° with the longitudinal axis of the elongate housing 100. The lumen in each suture mount 144 can also be at an angle. When the first and second tissue grasping arms 130, 140 have pinched the two leaflets 20A, 20B together in a closed configuration, the angled needle guide tracks 113 and the lumens of the suture mounts 144 can be substantially aligned or coaxial so that needles 160 can be deployed along a curved trajectory alongside or through the first grasping arm 130, through the grasped two leaflets 20A, 20B, and catch suture portions located at the suture mounts 144.

A method of suturing anatomical valves, such as repair of mitral valve leaflets 20A, 20B, is illustrated in FIGS. 14A-14H. Using the sheath 12 of FIG. 1 as described above, the tissue-engaging distal assembly of the suturing device 100 can be advanced toward the mitral valve through an apex of the heart. The suturing device 100 can be advanced with the first and second tissue grasping arms 130, 140 in a closed configuration to allow the tissue-engaging distal assembly to be advanced through the sheath 12. The longitudinal axis of the suturing device 100 and the direction of approach are generally aligned with the direction of blood flow through the native valve. When the tissue-engaging distal assembly is approaching the mitral valve or after the tissue-engaging distal assembly has reached the mitral valve, the first and second tissue grasping arms 130, 140 can be transitioned to an open configuration in a manner as described above. The method of suturing mitral leaflets as illustrated in FIGS. 14A-14H can advantageously avoid maneuvering the tissue grasping arms and the distal end of the elongate housing among the chordae tendineae. This can simplify the suturing procedure and reduce trauma to the patient.

Figure 14A:
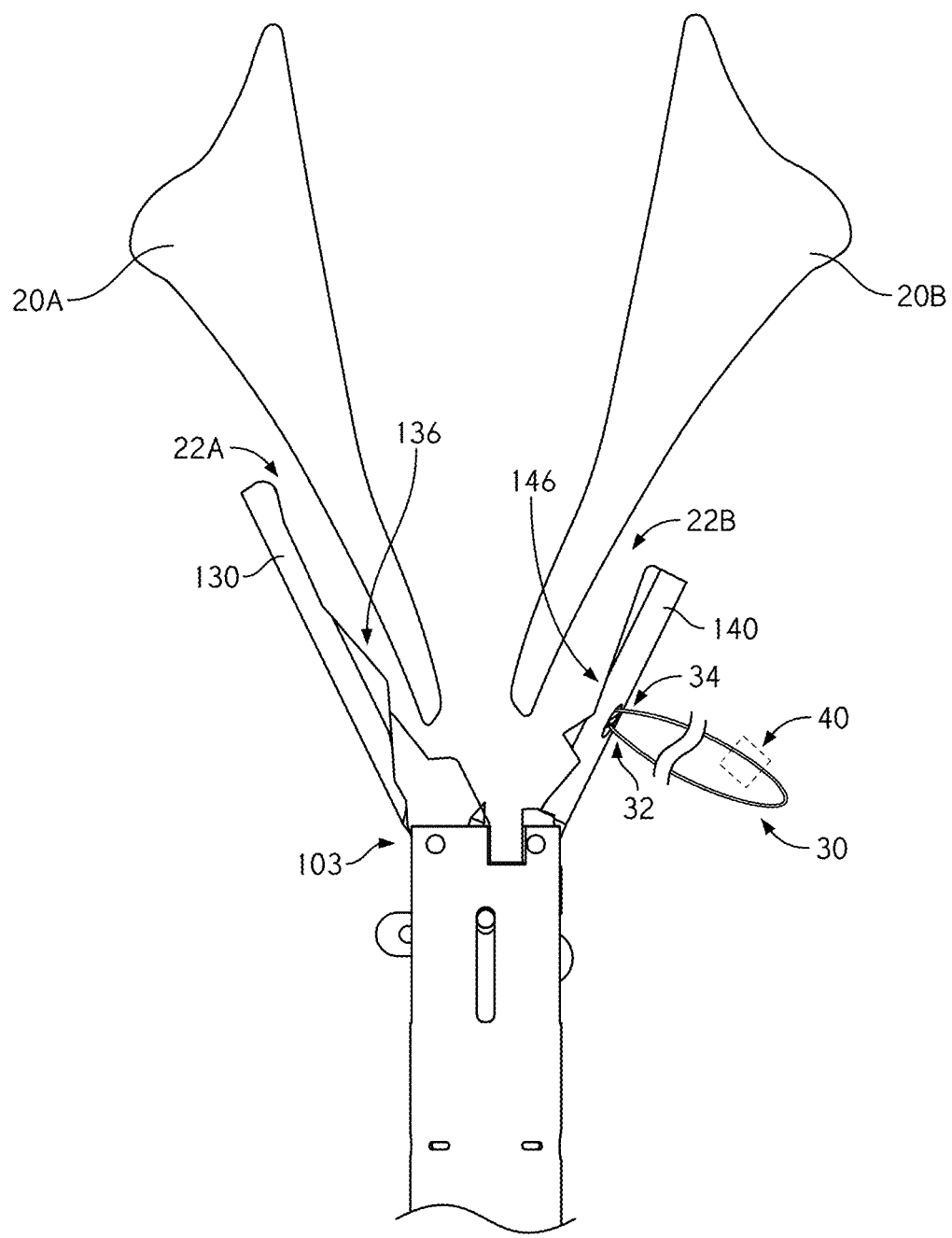
FIGS. 14A-14H illustrate example methods of suturing a biological valve using a suturing system including the suturing device of FIG. 4A.

As shown in FIG. 14A, tissue-facing surfaces 136, 146 of the first and second arms 130, 140 can be placed near or adjacent the suturing device facing surfaces 22A, 22B of the leaflets 20A, 20B. The single suture strand 30 can be pre-loaded on the suturing device 100. Specifically, each end 32, 34 of the suture strand 30 can be mounted onto one of the suture mounts 144. A pledget 40 can optionally be pre-loaded on the suture strand 30. The suture strand 30 can be held in a suture spool on the suturing device 100. The suture spool can be mounted in fixed relationship to and located external to the elongate housing 110 and the handle 120. The suture spool can be configured to retain a portion of the suture strand. When the suture portions of the suture strand loaded on the suture mounts 144 are captured by the needles and the needles bring the captured suture portions through the tissue, the suture spool can be configured such that the suture strand unwinds from the suture spool. Examples of a spool are described in International Patent Application No. PCT/US2016/026965, entitled "SUTURING SPOOLS FOR TISSUE SUTURING DEVICE" and filed on Apr. 11, 2016, which are incorporated herein by reference in its entirety.

Figure 14B:
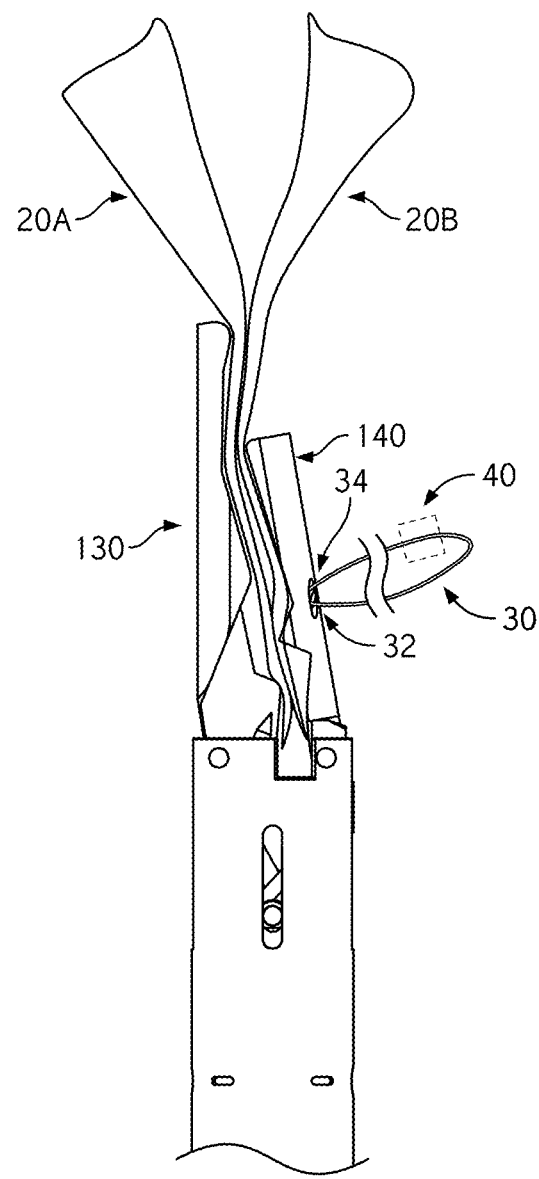

As shown in FIG. 14B, once a desired orientation of the first and second tissue grasping arms 130, 140 relative to the leaflets 20A, 20B is reached, the first and second tissue grasping arms 130, 140 can transition back to the closed configuration in a manner described above to grasp the leaflets 20A, 20B. The tissue-facing surfaces 136, 146 of the first and second tissue grasping arms 130, 140 can contact the suturing device facing surfaces 22A, 22B of the leaflets 20A, 20B. As described above, the suturing device 100 can optionally transition into the grip configuration to more firmly clamp onto the two leaflets. If the user is unsatisfied with the way the leaflets 20A, 20B are grasped by the first and second tissue grasping arms 130, 140, the first and second tissue grasping arms 130, 140 can return to the open configuration as shown in FIG. 14A for being repositioned relative to the leaflets 20A, 20B.

Figure 14C:
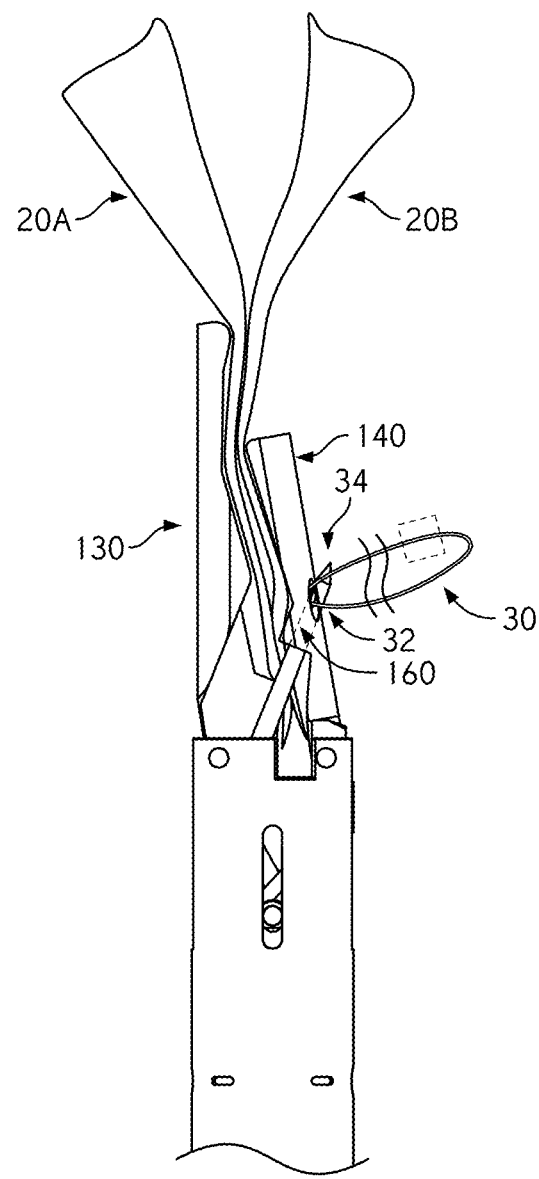
Figure 14D:
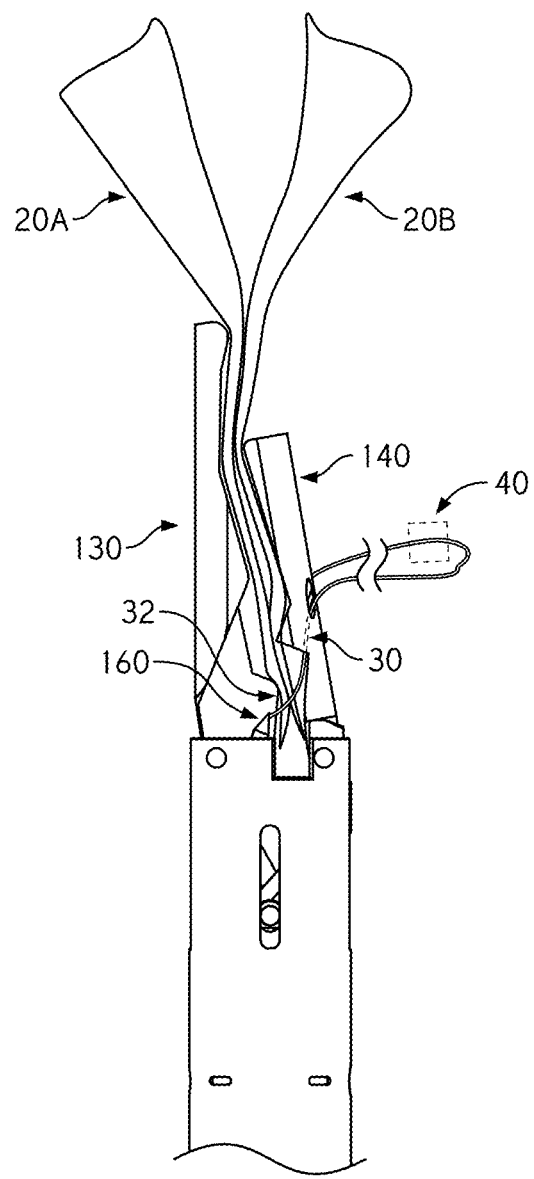

In FIG. 14C, once the user determines that the leaflets 20A, 20B between the first and second arms 130, 140 are properly aligned, the needles 160 can be deployed in a manner as described above. The suturing device 100 described above can deploy the two needles simultaneously. The suturing device can also be configured to deploy each needle sequentially, or have both options, based on the disclosure herein. The needles 160 can engage the suture portions, which can be the two ends 32, 34 of the single suture strand 30. As described above, when the user lets go of the slide 122 on the handle 120, the distal spring 126 can bias the slide 122 proximally, thereby retracting the needles 160 back into the elongate housing 100. As shown in FIG. 14D, the suture ends 32, 34 captured by the needles 160 can follow the needles 160 through the second tissue grasping arm 140 via the suture mount 144, the leaflets 20A, 20B, and into the elongate housing.

Figure 14E:
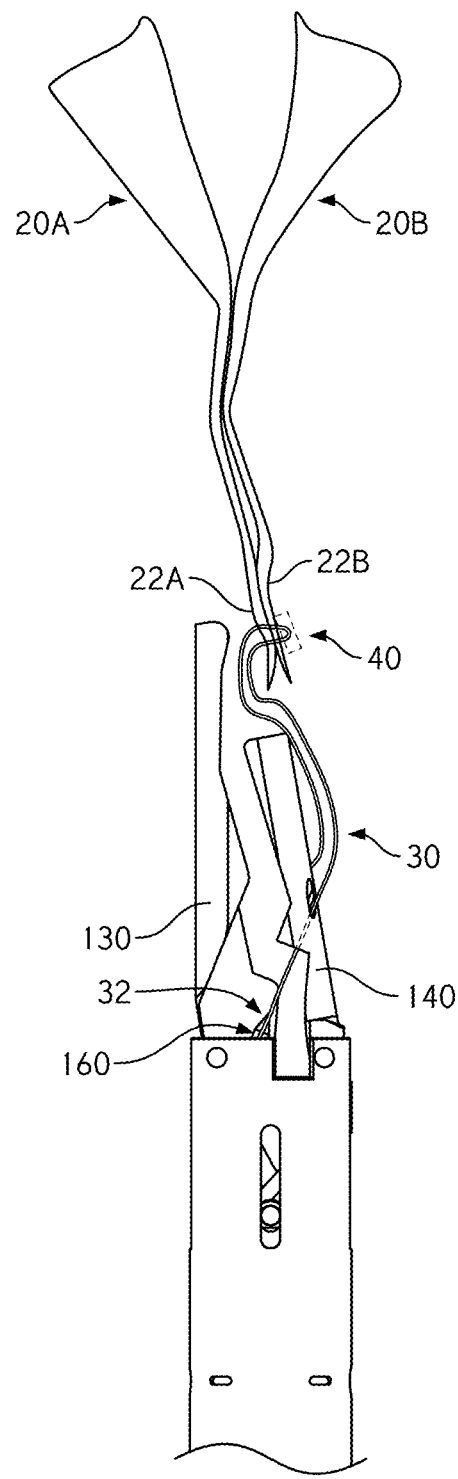
Figure 14F:
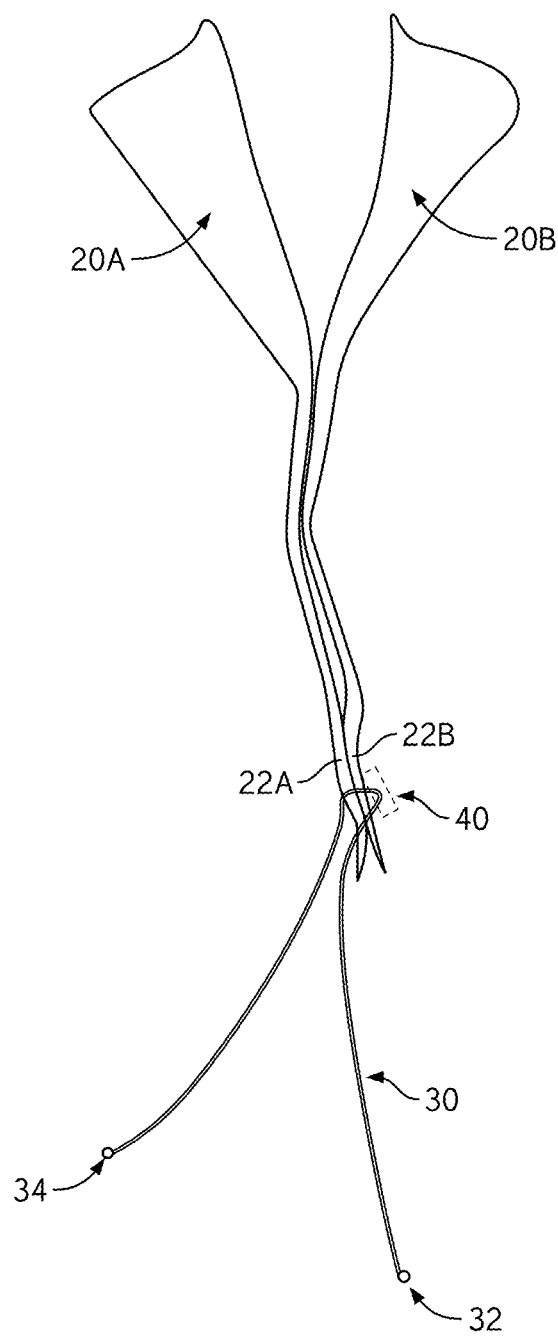
Figure 14G:
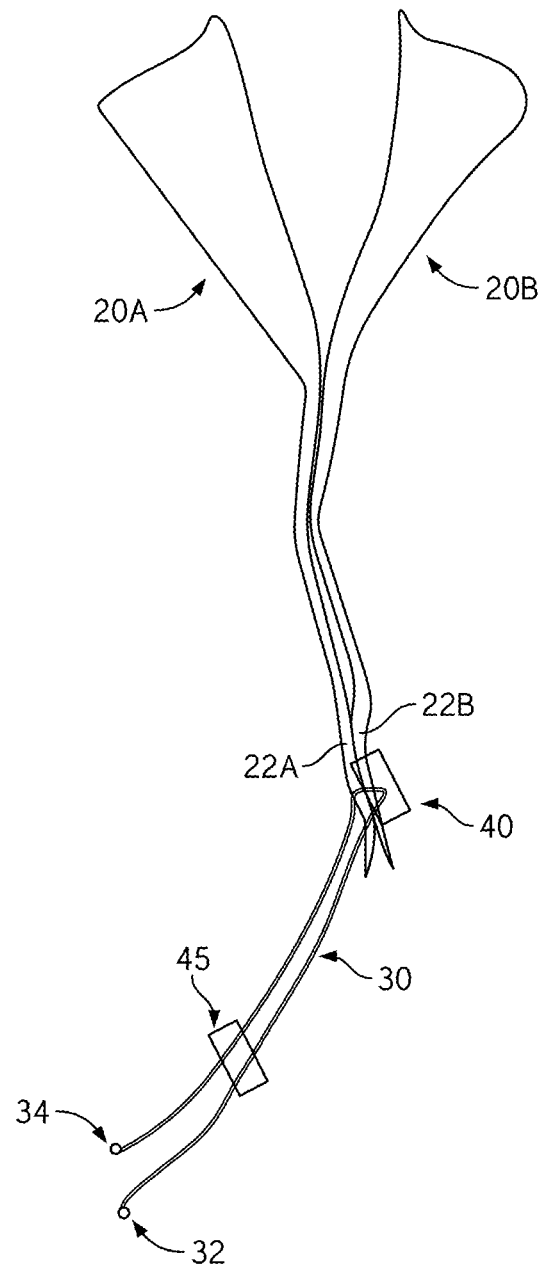

As shown in FIG. 14E, when the suturing device 100 is retracted proximally to be removed from the patient's body, the two ends 32, 34 of the suture strand 30 can continue to follow the suturing device 100. Prior to removal from the patient's body, the user may actuate the handle to open the tissue grasping arms to release the native leaflets. The tissue grasping arms can also be re-closed before removing the arms from the suturing location, here the left ventricle of the heart. Re-closing the tissue grasping arms can reduce the profile of the suturing device 100 and make it easier to retract the suturing device from the patient's body. As shown in FIG. 14F, once the suturing device 100 is removed from the patient's body, the ends 32, 34 of the suture strand 30 can be disengaged from the needles 160. The suture ends 32, 34 can be pulled to bring the leaflets 20A, 20B together. Pulling the suture ends 32, 34 can also pull the pledget 40 against or into contact with the suturing device facing surface 22B of the leaflet 20B. As shown in FIG. 13G, a second pledget 45 can optionally be passed through the two ends 32, 34 of the suture strand 30. The second pledget 45 can be pushed against or into contact with the suturing device facing surface 22A of the leaflet 20A. In some embodiments, the suture 30 placed through the leaflets may be an initial suture that is used to then guide an additional suture through the sutured tissue. In such embodiments, the initial suture is removed from the patient and the additional suture is used to draw the leaflets together.

Figure 14H:
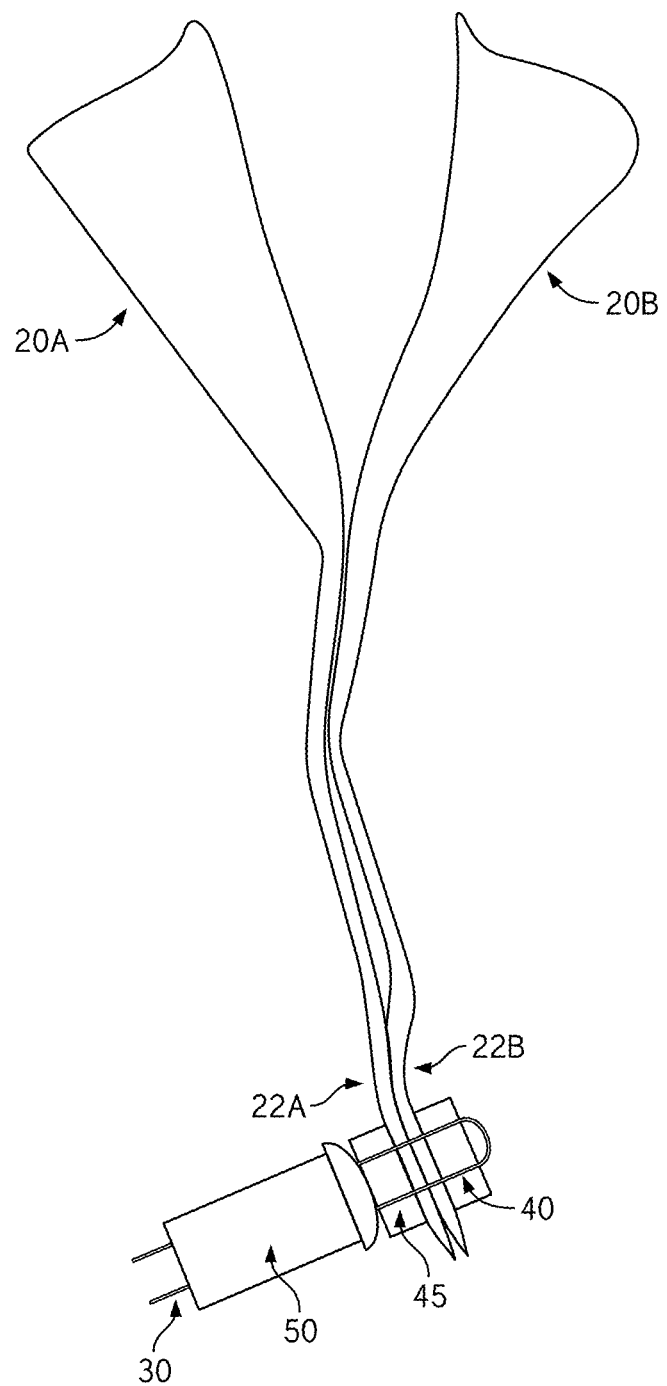

Turning to FIG. 14H, a knot 50 can be formed with the suture ends 32, 34. Any suitable knot may be tied by the user. In some embodiments, A knot-forming device to form a knot as shown in FIG. 3. The knot 50 can include a knot body and a plug. Ends of the suture strand 30 can be passed through a lumen of the knot body. The knot body can be advanced to the suturing site, for example, also through the sheath 12 of FIG. 1. The second pledget 45 can be threaded onto the suture ends 32, 34 before applying the knot. The second pledget 45 can be pushed with the knot body to be pressed against the suturing device facing surface 22A of the leaflet 20A. The plug can be advanced into the lumen of the plug body. The plug can be dimensioned to have an interference fit with the lumen of the plug body. The suture strand 30 can be jammed between the lumen of the knot body and the plug to form the knot 50. The knot body and the plug can be housed in a distal end of the knot-forming device and can be ejected from the distal end of the knot-forming device after forming the knot 50. Examples of a knot-forming device are described in in U.S. patent application Ser. No. 13/905,225, entitled "METHOD AND APPARATUS FOR APPLYING A KNOT TO A SUTURE" and filed on Aug. 14, 2006, now U.S. Pat. No. 9,642,616, which is incorporated herein by reference in its entirety. The knot can be formed on the device facing surface 22A of the leaflet 20A. To form a knot by hand, the user can then tie a knot outside the patient's body and pass the knot to the device facing surface 22A of the leaflet 20A.

Suturing Devices with Other Needle-Suture Mount Alignment Features

Suturing devices with other ways for aligning the needles and the suture mounts will now be described. These suturing devices can incorporate features of the suturing device 100 of FIG. 4A, except as described below.

Figure 17A:
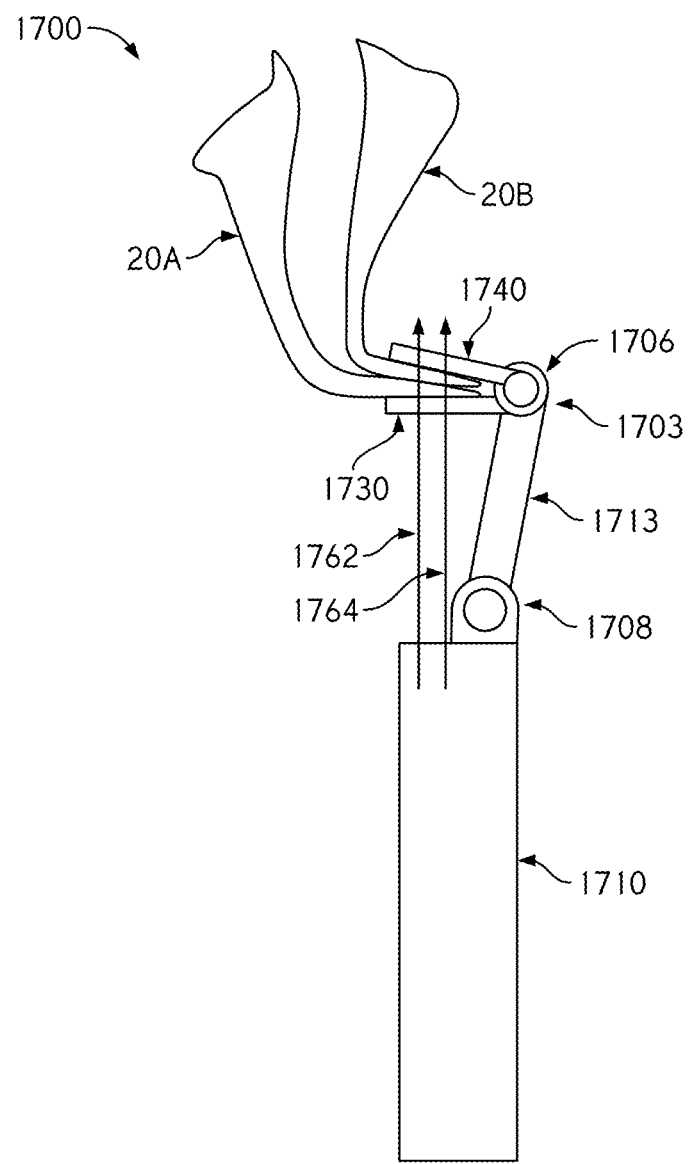
FIG. 17A illustrates schematically an embodiment of a distal end of a suturing device for suturing a biological valve.
Figure 17B:
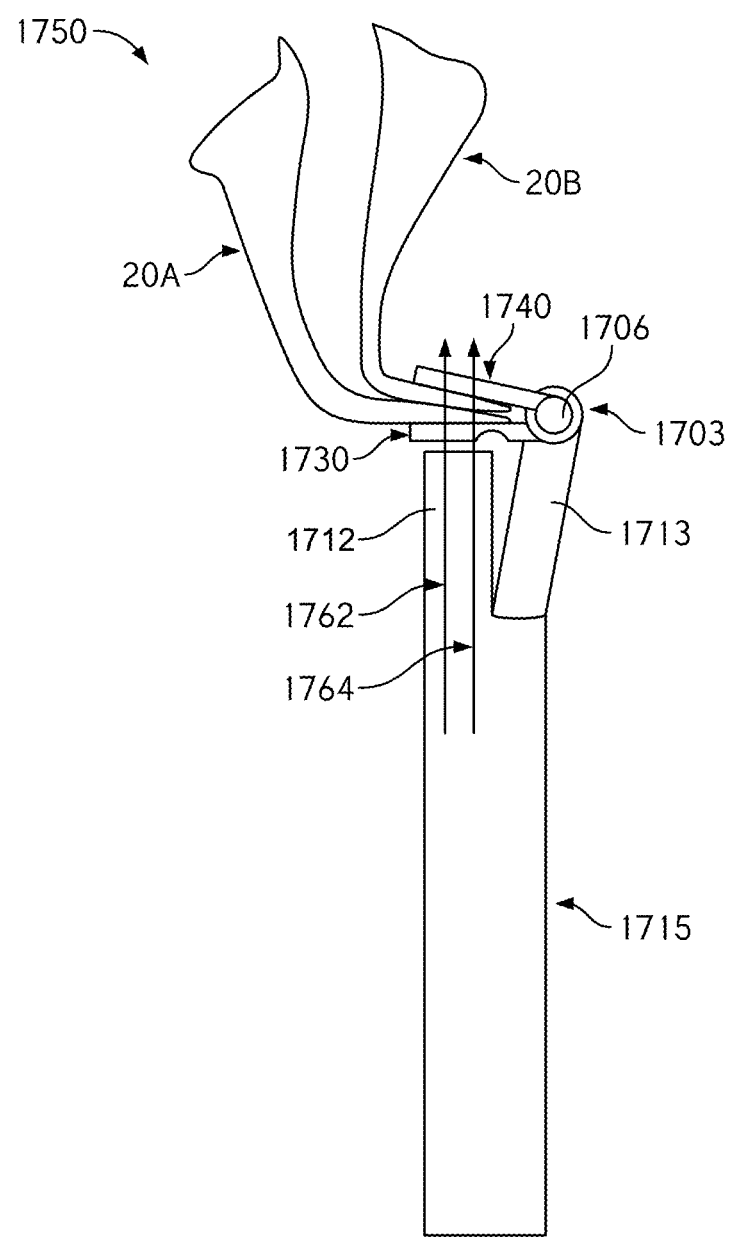
FIG. 17B illustrates schematically an embodiment of a distal end of a suturing device for suturing a biological valve.

FIGS. 17A and 17B illustrate embodiments of the suturing devices 1700, 1750 with one or more hinged joints that allow the first and second tissue grasping arms 1730, 1740, and optionally a distal portion of the elongate housing 1710, to rotate so as to manipulate tissue, for example, the leaflets 20A, 20B captured by the arms 1730, 1740 in different orientations than their natural positions.

As shown in FIG. 17A, the suturing device 1700 can have two hinged joints 1706, 1708. The joint 1706 can be located between the tissue grasping arms 1730, 1740 and the distal end 1703 of the elongate housing 1710. The joint 1708 can be located between a distal portion 1713 and the remaining portion of the elongate housing 1710. After the tissue grasping arms 1730, 1740 have captured the leaflets 20A, 20B between the arms 1730, 1740, the suturing device 1700 can bend at the two joints 1706, 1708 so that at least one of the tissue facing surfaces of the tissue grasping arms 1730, 1740 can be substantially perpendicular to the elongate housing 1710. This bending can orient the suture mounts on the second tissue grasping arm 1740, and the leaflets between the arms 1730, 1740, into the directions of movement of the needles indicated by arrows 1762, 1764. Similar to the suturing device 100 described above, the elongate housing 1710 can include at least two needle lumens. One needle can be housed in each needle lumen. The needle lumens of the suturing device 1700 can be straight and substantially parallel to the longitudinal axis of the elongate housing 1710. The needles each can be deployed using features similar to the slide 122 described above to engage suture portions retained at the suture mounts on the second tissue grasping arm 1740. The first tissue grasping arm 1730 can have a corresponding lumen or cut-out portion for each suture mount on the second tissue grasping arm 1740 so that the needles can travel through or past the first tissue grasping arm 1730 unhindered. The needles can be deployed simultaneously or sequentially.

FIG. 17B illustrates a variation 1750 of the suturing device 1700 of FIG. 17A and can incorporate the features of the suturing device 1700, except as described below. The suturing device 1750 can have one hinged joint 1706 between the tissue grasping arms 1730, 1740 and the distal end 1703 of the elongate housing 1715. The elongate housing 1715 can have a bifurcated needle lumens portion 1712 running alongside the distal portion 1713 of the elongate housing 1715. After the tissue grasping arms 1730, 1740 have captured the leaflets 20A, 20B between the arms 1730, 1740, the first and second arms 1730, 1740 can rotate at the joint 1706 toward the bifurcated needle lumens portion 1712. The rotation can stop when at least one of the tissue facing surfaces 1735, 1745 of the tissue grasping arms 1730, 1740 is substantially perpendicular to the bifurcated needle lumens portion 1712. This rotation can orient the suture mounts on the second tissue grasping arm 1740, and the leaflets between the arms 1730, 1740, into the directions of movement of the needles indicated by arrows 1762, 1764. The bifurcated needle lumens portion 1712 can include at least two needle lumens. One needle can be housed in each needle lumen. The needle lumens can be straight and substantially parallel to the longitudinal axis of the elongate housing 1715. The needles each can be deployed from the bifurcated needle lumens portion 1712 using features such as the slide 122 of FIG. 4A described above to engage suture portions retained at the suture mounts on the second tissue grasping arm 1740. The first tissue grasping arm 1730 can have a corresponding lumen or cut-out portion for each suture mount on the second tissue grasping arm 1740 so that the needles can travel through or past the first tissue grasping arm unhindered. The first tissue grasping arm 1730 can further have a detent 1735 on a surface opposite the tissue facing surface. The detent 1736 can be configured to better align the needles with the tissue grasping arms 1730, 1740, and therefore, with the suture mounts. The needles can be deployed simultaneously or sequentially.

Figure 18A:
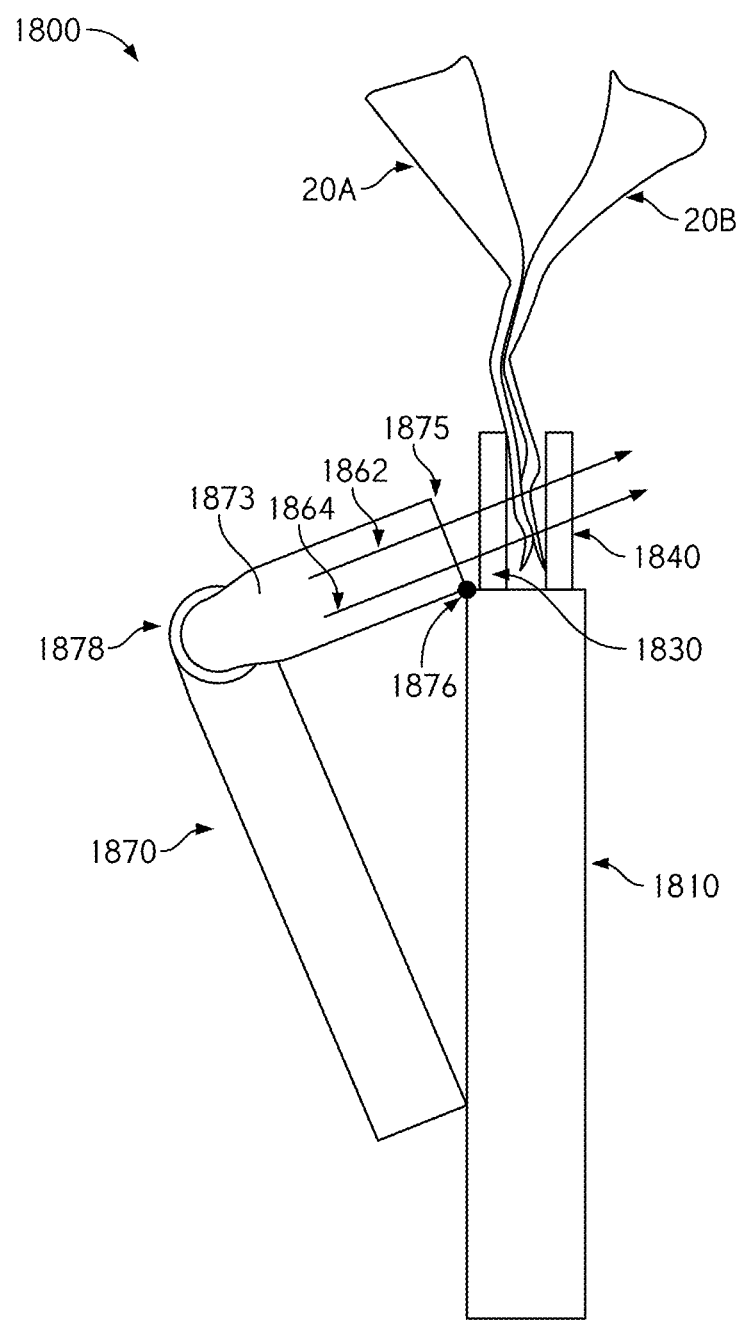
FIG. 18A illustrates schematically an embodiment of a distal end of a suturing device for suturing a biological valve.
Figure 18B:
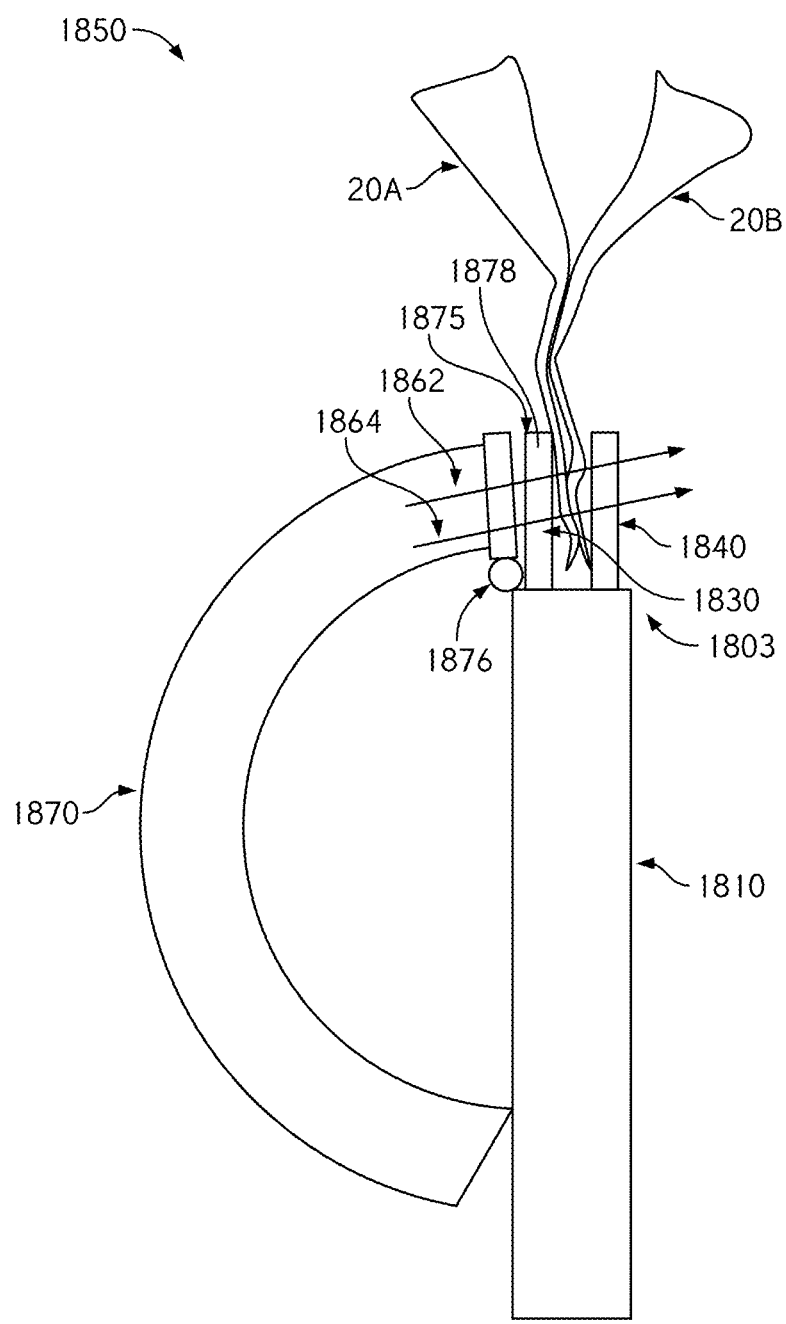
FIGS. 18B-18C illustrate schematically embodiments of a distal end of a suturing device for suturing a biological valve.
Figure 18C:
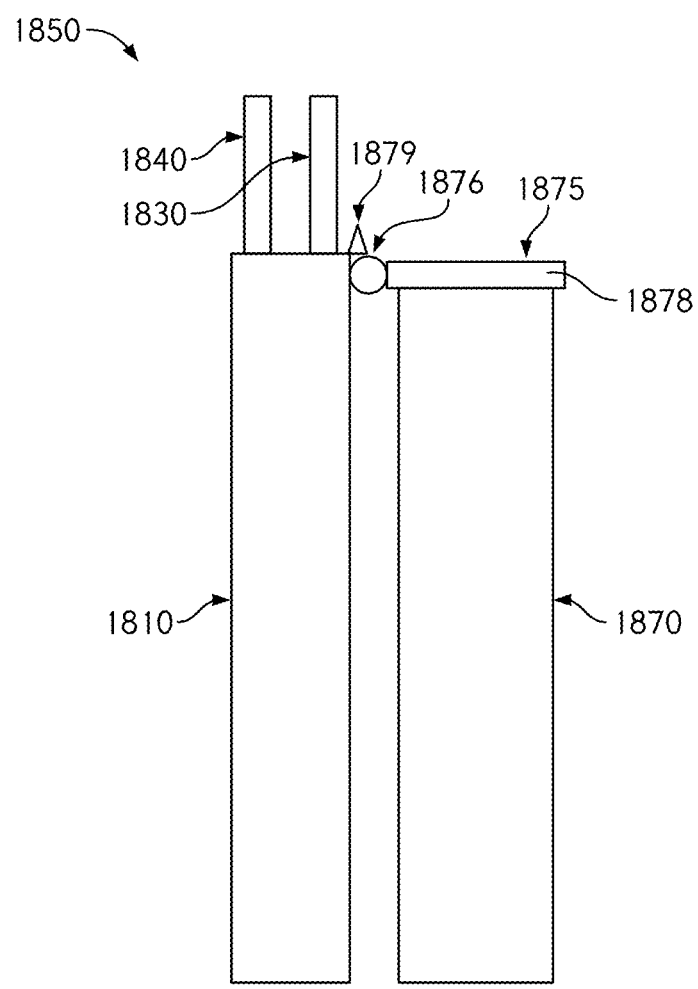

FIGS. 18A-18C illustrate embodiments of the suturing device 1800, 1850 with a deformable catheter running alongside the elongate housing 1810. As shown in FIG. 18A, the deformable catheter can be in the form of a catheter 1870 with a hinged joint 1878 along its length. A distal end of the catheter 1870 can be hingedly connected 1876 to the distal end 1803 of the elongate housing 1810. Because the distal end of the catheter 1870 is secured to the hinged connection 1876, a distal force can buckle the catheter 1870 at the hinged joint 1878 outward away from the longitudinal axis of the elongate housing 1810. The catheter 1870 can run alongside at least a portion of the elongate housing 1810. The catheter 1870 can have a distally facing opening 1875. The outward buckling can allow the distally facing opening 1875 to be at an angle or substantially parallel to the longitudinal axis of the elongate housing 1810. A distal portion 1873 of the catheter 1870 that is immediately proximal of the distally facing opening 1875 can include at least two needle lumens. One needle can be housed in each needle lumen. The needle lumens can be substantially straight and parallel to a longitudinal axis of the distal portion 1873. The outward bending can thus orient the directions of movement of the needles indicated by arrows 1862, 1864 to coincide with the suture mounts on the second tissue grasping arm 1840. The needles each can be deployed using features such as the slide 122 described above to engage a suture portion retained at the suture mount on the second tissue grasping arm 1840. The first tissue grasping arm 1830 can have a corresponding lumen or cut-out portion for each suture mount on the second tissue grasping arm 1840 so that the needles can travel through or past the first tissue grasping arm unhindered. The needles can be deployed simultaneously or sequentially.

FIGS. 18B-18C illustrate a variation 1850 of the suturing device 1800 of FIG. 18A and can incorporate the features of the suturing device 1800, except as described below. The deformable catheter can be in the form of a catheter 1870 coupled to a ring or a hypotube 1878 at its distal end. The catheter 1870 can run alongside at least a portion of the elongate housing 1810. The ring or hypotube 1878 can be hingedly connected 1876 to the distal end 1803 of the elongate housing 1810. The catheter 1870 as shown in FIG. 18A can also be coupled to a hypotube at its distal end. The ring or hypotube 1878 can have a distally facing opening 1875. When the tissue grasping arms 1830, 1840 have captured the two leaflets 20A, 20B, a force can be applied from a proximal end of the catheter 1870 to its distal end. The force can be applied by a push sleeve. Because the ring or hypotube 1878 is secured to the hinged connection 1876, the distal force can force the catheter 1870 to flex and bulge outward away from the longitudinal axis of the elongate housing 1810. The outward bulging can allow the distally facing opening 1875 to be at an angle or substantially parallel to the longitudinal axis of the elongate housing 1810. The catheter 1870 can include at least two needle lumens. One needle can be housed in each needle lumen. The needle lumens can be substantially straight and parallel to a longitudinal axis of the catheter 1870. The outward bulging can thus orient the directions of movement of the needles as indicated by arrows 1862, 1864 to coincide with the suture mounts on the second tissue grasping arm 1840. The needles each can be deployed using features such as the slide 122 described above to engage suture portions retained at the suture mounts on the second tissue grasping arm 1840. The first tissue grasping arm 1830 can have a corresponding lumen or cut-out portion for each suture mount on the second tissue grasping arm 1840 so that the needles can travel through or past the first tissue grasping arm unhindered. The needles can be deployed simultaneously or sequentially.

As shown in FIG. 18C, the suturing device 1850 can further include a stopper 1879, such as a raised ridge or a small protrusion, at or near the hinged connection 1876. The stopper 1879 can be configured to limit the amount of flexing of the catheter 1870.

The suturing devices shown in FIGS. 18A-18C, and also shown in FIGS. 4A-13E, can advantageously avoid the need to tug and manipulate the leaflets into a different plane than that of their natural orientations and positions.

From the foregoing description, it will be appreciated that inventive suturing devices and methods are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are not drawn to scale, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method of suturing anatomical tissue, comprising:
   grasping adjacent portions of the tissue to be sutured between a first movable grasping arm and a second movable grasping arm of a delivery device by transitioning the first and second grasping arms from an open configuration to a closed configuration, wherein the second grasping arm comprises a first suture mount and second suture mount for holding portions of one or more sutures on a first side of the tissue to be sutured, the delivery device further carrying a first needle and a second needle, wherein respective distal tips of the first and second grasping arms are moved toward each other and toward a longitudinal axis of the delivery device when transitioning from the open configuration to the closed configuration;
   advancing the first needle and the second needle of the delivery device through the grasped portions of the tissue to be sutured from a second side of the tissue to be sutured opposite to the first side to catch the portions of the one or more sutures held in the first and second suture mounts, respectively, the first and second needles being advanced parallel to the longitudinal axis of the delivery device while the adjacent portions of the tissue to be sutured between the first and second grasping arms are held in an orientation generally perpendicular to the longitudinal axis; and
   retracting the first and second needles from the first and second suture mounts to carry the suture portions back through grasped portions of the tissue to be sutured such that the one or more sutures extend through the portions of the tissue to be sutured.

2. The method of claim 1, further comprising aligning the first and second needles and the adjacent portions of the tissue to be sutured grasped therebetween with the first and second suture mounts.

3. The method of claim 1, further comprising using the one or more sutures extending through the portions of the tissue to be sutured and/or one or more subsequently placed sutures to secure the portions of the tissue to be sutured relative to each other by pulling on one or both of the suture ends to draw the suture tight against the first side of the tissue.

4. The method of claim 3, further comprising applying a knot to the one or more sutures and/or the one or more subsequently placed sutures.

5. The method of claim 4, wherein the knot is applied from the first side of the tissue to be sutured.

6. The method of claim 4, wherein the tissue to be sutured is not being grasped when the knot is applied.

7. The method of claim 1, wherein the first and second needles are deployed and/or retracted simultaneously or sequentially.

8. The method of claim 1, wherein the first and second grasping arms and the needles are provided on a suturing device controlled by a single handle operated from outside of a patient's body.

9. The method of claim 1, further comprising drawing a first pledget carried by the one or more suture portions extending through the portions of the tissue to be sutured into contact with the first side of the tissue to be sutured.

10. The method of claim 9, further comprising delivering a second pledget along the one or more suture portions extending through the portions of the tissue to be sutured into contact with the second side of the tissue to be sutured.

11. The method of claim 1, wherein the tissue to be sutured is a mitral valve.

* * * * *